(12) United States Patent
Baasov et al.

(10) Patent No.: US 10,576,095 B2
(45) Date of Patent: *Mar. 3, 2020

(54) USE OF AMINOGLYCOSIDE ANALOGS IN THE TREATMENT OF RETT SYNDROME

(71) Applicant: Eloxx Pharmaceuticals Ltd., Rehovot (IL)

(72) Inventors: Timor Baasov, Haifa (IL); Shmuel Tuvia, Natania (IL); Dori Pelled, Hod-HaSharon (IL)

(73) Assignee: ELOXX PHARMACEUTICALS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/258,735

(22) Filed: Jan. 28, 2019

(65) Prior Publication Data

US 2019/0183915 A1    Jun. 20, 2019

Related U.S. Application Data

(63) Continuation of application No. 15/316,209, filed as application No. PCT/IL2015/050573 on Jun. 4, 2015, now abandoned.

(60) Provisional application No. 62/008,028, filed on Jun. 5, 2014.

(51) Int. Cl.
     *A61K 31/7036* (2006.01)
(52) U.S. Cl.
     CPC .............. *A61K 31/7036* (2013.01)
(58) Field of Classification Search
     None
     See application file for complete search history.

(56) References Cited

U.S. PATENT DOCUMENTS

| | | | | |
|---|---|---|---|---|
| 8,895,519 | B2 * | 11/2014 | Baasov | C07H 5/06 514/38 |
| 9,175,029 | B2 * | 11/2015 | Baasov | C07H 5/06 |
| 9,616,079 | B2 * | 4/2017 | Baasov | C07H 5/06 |
| 9,943,533 | B2 * | 4/2018 | Baasov | C07H 5/06 |
| 2006/0194257 | A1 * | 8/2006 | Minassian | C07K 14/47 435/7.1 |
| 2013/0237489 | A1 | 9/2013 | Baasov et al. | |
| 2014/0357590 | A1 | 12/2014 | Baasov et al. | |
| 2016/0074425 | A1 | 3/2016 | Baasov et al. | |
| 2017/0182078 | A1 | 6/2017 | Baasov et al. | |
| 2017/0360817 | A1 | 12/2017 | Baasov et al. | |
| 2018/0200276 | A1 | 7/2018 | Baasov et al. | |

FOREIGN PATENT DOCUMENTS

| | | |
|---|---|---|
| EP | 3296311 | 3/2018 |
| JP | 2009-532461 | 9/2009 |
| JP | 2013-542981 | 11/2013 |
| JP | 5960712 | 11/2013 |
| JP | 2016-121168 | 7/2016 |
| WO | WO 2007/113841 | 10/2007 |
| WO | WO 2012/066546 | 5/2012 |
| WO | WO 2015/186134 | 12/2015 |

OTHER PUBLICATIONS

Communication Pursuant to Article 94(3) EPC dated Aug. 23, 2016 From the European Patent Office Re. Application No. 11799501.9.
Communication Pursuant to Article 94(3) EPC dated May 29, 2015 From the European Patent Office Re. Application No. 11799501.9.
European Search Report and the European Search Opinion dated Dec. 22, 2017 From the European Patent Office Re. Application No. 17192028.3. (12 Pages).
Examination Report Under Sections 12 & 13 of the Patents Act, 1970 and the Patents Rules, 2003 dated Mar. 5, 2018 From the Government of India, Intellectual Property India, Patents, Designs, Trade Marks, Geographical Indications Re. Application No. 876/MUMNP/2013. (6 Pages).
International Preliminary Report on Patentability dated Dec. 15, 2016 From the International Bureau of WIPO Re. Application No. PCT/IL2015/050573. (10 Pages).
International Search Report and the Written Opinion dated Sep. 1, 2015 From the International Searching Authority Re. Application No. PCT/IL2015/050573.
International Search Report and the Written Opinion dated Mar. 27, 2012 From the International Searching Authority Re. Application No. PCT/IL2011/000889.
Notice of Reason for Rejection dated Feb. 1, 2019 From the Japan Patent Office Re. Application No. 2018-036281 and Its Translation Into English. (6 Pages).

(Continued)

*Primary Examiner* — Traviss C McIntosh, III
(74) *Attorney, Agent, or Firm* — Perkins Coie LLP; Patrick D. Morris

(57) ABSTRACT

Compounds, methods and uses of pseudo-trisaccharide aminoglycosides represented by the general formula I:

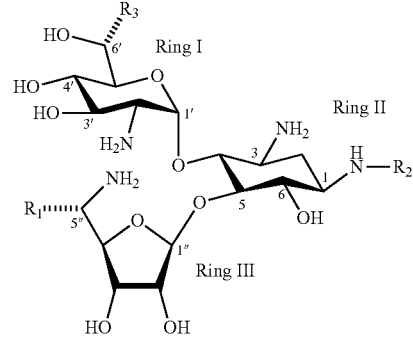

Formula I or a pharmaceutically acceptable salt thereof, wherein $R_1$ is selected from the group consisting of alkyl, cycloalkyl and aryl; and all other variables and features are as described in the specification, in the treatment of Rett syndrome are disclosed.

30 Claims, 8 Drawing Sheets
(8 of 8 Drawing Sheet(s) Filed in Color)

(56) References Cited

OTHER PUBLICATIONS

Notice of Reason for Rejection dated Feb. 17, 2017 From the Japan Patent Office Re. Application No. 2016-11038 and Its Translation Into English. (4 Pages).
Notice of Reason for Rejection dated Oct. 30, 2015 From the Japanese Patent Office Re. Application No. 2013-539397 and Its Translation Into English.
Office Action dated Feb. 6, 2019 From the Israel Patent Office Re. Application No. 249402 and Its Translation Into English. (6 Pages).
Office Action dated Jan. 18, 2018 From the Israel Patent Office Re. Application No. 226390. (2 Pages).
Official Action dated Aug. 11, 2016 From the U.S. Appl. No. 14/866,960.
Official Action dated Jan. 16, 2015 From the U.S. Appl. No. 14/461,477.
Official Action dated Feb. 18, 2014 From the U.S. Appl. No. 13/885,715.
Official Action dated Apr. 19, 2018 From the U.S. Appl. No. 15/914,045. (20 pages).
Official Action dated Apr. 21, 2017 from the U.S. Appl. No. 15/453,990.
Official Action dated Jul. 27, 2018 From the U.S. Appl. No. 15/316,209. (32 pages).
Official Decision of Rejection dated Nov. 7, 2017 From the Japan Patent Office Re. Application No. 2016-11038 and Its Translation Into English. (4 Pages).
Requisition by the Examiner dated Sep. 21, 2017 From the Innovation, Science and Economic Development Canada, Canadian Intellectual Property Office Re. Application No. 2,816,789. (16 Pages).
Translation of Office Action dated Jan. 18, 2018 From the Israel Patent Office Re. Application No. 226390. (2 Pages).
Azimov et al. "G418-Mediated Ribosomal Read-Through of A Nonsense Mutation Causing Autosomal Recessive Proximal Renal Tubular Acidosis", American Journal of Physiology, Renal Physiology, 295(3): F633-F641, Sep. 2008.
Brendel et al. "Readthrough of Nonsense Mutations in Rett Syndrome: Evaluation of Novel Aminoglycosides and Generation of A New Mouse Model", Journal of Molecular Medicine, 89(4): 389-398, Published Online Dec. 1, 2010.
Brendel et al. "Readthrough of Nonsense Mutations in Rett Syndrome: Evaluation of Novel Aminoglycosides and Generation of A New Mouse Model", Journal of Molecular Medicine, XP019889972, 89(4): 389-398, Published Online Dec. 1, 2010. Abstract, p. 397, col. 1-h, Para 2-3.
Brendel et al. "Suppression of Nonsense Mutations in Rett Syndrome by Aminoglycoside Antibiotics", Pediatric Research, XP055209334, 65(5): 520-523, May 1, 2009. Abstract.
Goldmann et al. "Beneficial Read-Through of A USH1C Nonsense Mutation by Designed Aminoglycoside NB30 in the Retina", Investigative Ophthalmology & Visual Science, 51(12): 6671-6680, Dec. 2010.
Hainrichson et al. "Designer Aminoglycosides: The Race to Develop Improved Antibiotics and Compounds for the Treatment of Human Genetic Diseases", Organic and Biomolecular Chemistry, 6(2): 227-239, Jan. 21, 2008.
Hobbie et al. "Engineering the rRNA Decoding Site of Eukaryotic Cytosolic Ribosomes in Bacteria", Nucleic Acids Research, 35(18): 6086-6093, Aug. 30, 2007.
Hobbie et al. "Genetic Analysis of Interactions With Eukayotic rRNA Identify the Mitoribosome as Target in Aminoglycoside Ototoxicity", Proc. Natl. Acad. Sci. USA, PNAS, 105(52): 20888-20893, Dec. 30, 2008.
Hobbie et al. "Mitochondrial Deafness Alleles Confer Misreading of the Genetic Code", Proc. Natl. Acad. Sci. USA, PNAS, 105(9): 3244-3249, Mar. 4, 2008.
Kandasamy et al. "Increased Selectivity Toward Cytoplasmic Versus Mitochondrial Ribosome Confers Improved Efficiency of Synthetic Aminoglycosides in Fixing Damaged Genes: A Strategy for Treatment of Genetic Diseases Caused by Nonsense Mutations", Journal of Medicinal Chemistry, XP055209352, 55(23): 10630-10643, Nov. 13, 2012. Abstract, Fig.2, p. 10637, col. r-h, Para 4-5.
Kandasamy et al. "Repairing Faulty Genes by Aminoglycosides: Identification of New Pharmacophore With Enhanced Suppression of Disease-Causing Nonsense Mutations", MedChemComm, XP055209402, 2(3): 165-171, Jan. 14, 2011. Figs.1-3, Table 1, Abstract.
Keeling et al. "Pharmacological Suppression of Premature Stop Mutations That Cause Genetic Diseases", Current Pharmacogenomics, 3(4): 259-269, 2005.
Keeling et al. "Suppression of Nonsense Mutations as a Therapeutic Approach to Treat Genetic Diseases", RNA. 2: 837-852, Nov./Dec. 2011.
Kerem "Pharmacologic Therapy for Stop Mutations: How Much CFTR Activity is Enough?", Current Opinion in Pulmonary Medicine, 10: 547-552, 2004.
Kondo et al. "Differential Selectivity of Natural and Synthetic Aminoglycosides Towards the Eukaryotic and Prokaryotic Decoding A Sites", ChemBioChem, 8: 1700-1709, 2007.
Linde et al. "Introducing Sense Into Nonsense in Treatments of Human Genetic Diseases", Trends in Genetics, 24(11): 552-563, Oct. 18, 2008.
Lopez-Novoa et al. "New Insights Into the Mechanism of Aminoglycoside Nephrotoxicity: An Integrative Point of View", Kidney International, Online Publication, 79(1): 33-45, Sep. 22, 2010.
Malik et al. "Aminoglycoside-Induced Mutation Suppression (Stop Codon Readthrough) as A Therapeutic Strategy for Duchenne Muscular Dystrophy", Therapeutic Advances in Neurological Disorders, 3(3): 379-389, Nov. 2010.
Nudelman "Combined Chemical-Enzymatic Assembly of Aminoglycoside Derivatives With N-1-AHB Side Chain", Advanced Synthesis & Catalysis, 350(11-12): 1682-1688, 2008.
Nudelman et al. "Development of Novel Aminoglycoside (NB54) With Reduced Toxicity and Enhanced Suppression of Disease-Causing Premature Stop Mutations", Journal of Medicinal Chemistry, 52(9): 2836-2845, 2009.
Nudelman et al. "Redesign of Aminoglycosides for Treatment of Human Genetic Diseases Caused by Premature Stop Mutations", Bioorganic & Medicinal Chemistry Letters, 16(24): 6310-6315, Dec. 15, 2006.
Nudelman et al. "Repairing Faulty Genes by Aminoglycosides: Development of New Derivatives of Geneticin (G418) With Enhanced Suppression of Diseases-Causing Nonsense Mutations", Bioorganic & Medicinal Chemistry, XP055017979, 18(11): 3735-3746, Jun. 1, 2010. Abstract, p. 3736, Compounds 1-2, 7-8, p. 3738, Compounds 11-16, Fig.1.
Pitcher et al. "Rett Syndrome Like Phenotypes in the R255X Mecp2 Mutant Mouse Are Rescued by MECP2 Transgene", Human Molecular Genetics, 24(9): 2662-2672, Advance Access Published Jan. 29, 2015.
Pokrovskaya et al. "Aminoglycosides: Redesign Strategies for Improved Antibiotics and Compounds for Treatment of Human Genetic Diseases", Methods in Enzymology, 478(Chap.21): 437-462, 2010.
Rebibo-Sabbah et al. "In Vitro and Ex Vivo Suppressing by Aminoglycosides of PCDH15 Nonsense Mutations Underlying Type 1 Usher Syndrome", Human Genetics, 122: 373-381, 2007.
Vecsler et al. "Ex Vivo Treatment With A Novel Synthetic Aminoglycoside NB54 in Primary Fibroblasts From Rett Syndrome Patients Suppresses MECP2 Nonsense Mutations", PLoS One, XP055209360, 6(6): e20733-1-e20733-8, Jun. 13, 2011.
Venkataraman et al. "Reawakening Retrocyclins: Ancestral Human Defensins Active Against HIV-1", PLoS Biology, 7(4/e1000095): 0720-0729, Apr. 2009.
Warchol "Cellular Mechanisms of Aminoglycoside of Aminoglycoside Ototoxicity", Current Opinion in Otolaryngology & Head and Neck Surgery, 18(5): 454-458, Oct. 2010.
Wegener et al. "Characterization of the MeCP2[R168X] Knockin Mouse Model for Rett Syndrome", PLOS One, 9(12): e0115444-1-e0115444-14, Dec. 26, 2014.

(56) References Cited

OTHER PUBLICATIONS

Xue et al. "Synthetic Aminoglycosides Efficiently Suppress Cystic Fibrosis Transmembrane Conductance Regulator Nonsense Mutations and Are Enhanced by Ivacaftor", American Journal of Respiratory Cell and Molecular Biology, XP055209395, 50(4): 805-816, Nov. 19, 2013. Abstract, Fig.1, p. 806, col. 3, Para 1.
Notice of Reason for Rejection dated Mar. 5, 2019 From the Japan Patent Office Re. Application No. 2016-571284 and Its Translation Into English. (6 Pages).
Vecsleer et al. "Ex Vivo Treatment with a Novel Synthetic Aminoglycoside NB54 in Primary Fibroblasts from Rett Syndrome Patients Suppresses MECP2 Nonsense Mutations", PLos One, 6(6), e20733: 1-8, Jun. 1, 2011.
European Patent Office, Article 94(3) Communication for European Patent Application No. 15735743.5. dated Oct. 4, 2019. 8 pages.
Indian Patent Office, Examination Report for Indian Patent Application No. 201627043334. dated Jul. 27, 2019. 7 pages.
Japanese Patent Office, Final Rejection for Japanese Patent Application No. 2016-571284. dated Nov. 5, 2019. 3 pages.
United States Patent & Trademark Office, Notice of Allowance for U.S. Appl. No. 13/885,715. dated Jul. 22, 2014.
United States Patent & Trademark Office, Notice of Allowance for U.S. Appl. No. 14/461,477. dated Jun. 26, 2015.
United States Patent & Trademark Office, Notice of Allowance for U.S. Appl. No. 14/866,960. dated Dec. 1, 2016.
Rowe et al. "Suppression of CFTR Termination Codons and Rescue of CFTR Protein and Function by the Synthetic Aminoglycoside NB54" American Journal of Respiratory Cell and Molecular Biology, 2010, pp. 1-43.

\* cited by examiner

USE OF AMINOGLYCOSIDE ANALOGS IN THE TREATMENT OF RETT SYNDROME

RELATED APPLICATIONS

This application is a continuation of U.S. patent application Ser. No. 15/316,209 filed on Dec. 5, 2016, which is a National Phase of PCT Patent Application No. PCT/IL2015/050573 having International Filing Date of Jun. 4, 2015, which claims the benefit of priority under 35 USC § 119(e) of U.S. Provisional Patent Application No. 62/008,028 filed on Jun. 5, 2014. The contents of the above applications are all incorporated by reference as if fully set forth herein in their entirety.

FIELD AND BACKGROUND OF THE INVENTION

The present invention, in some embodiments thereof, relates to therapy and, more particularly, but not exclusively, to compositions and methods utilizing aminoglycoside analogs in the treatment of Rett syndrome.

Rett syndrome (RTT, MIM 312750) is an X-linked postnatal neurodevelopmental disorder predominantly occurring in girls with a worldwide incidence of 1/10,000-15,000 female births. After normal development, during the first 6 to 18 months developmental stagnation and then regression occurs. During the phase of regression, purposeful hand use and language are lost while gross motor functions are relatively preserved. After the phase of regression the clinical picture remains stable for many years.

The major causative factor of RTT is deficiency of the X-linked methyl CpG-binding protein 2 (MeCP2) at Xq28, in which over 200 mutations have been identified so far in classical and atypical RTT patients. The majority of RTT causative mutations involve C.T transitions at the CpG hot-spots leading to missense, nonsense and frame-shift mutations, mostly originating de novo in the paternal germline. Phenotypic heterogeneity in RTT has been related, for the most part, to MECP2 mutation type and localization, as well as X chromosome inactivation (XCI) pattern.

The MECP2 gene encodes two isoform proteins, MeCP2_e1 and MeCP2_e2 products of an alternative initiation at exon 1 and splicing of exon 2, both of which are nuclear and co-localize with the methylated heterochromatin. Studies have shown that MeCP2 role in neurons is flexible and complex, as MeCP2 has been implicated in both repression and activation of a large number of genes, in modulation of RNA splicing, and has been suggested to affect global chromatin structure impacting on the entire neuronal genome.

Studies conducted with RTT mouse models showed that MeCP2 dysfunction in mature neurons accounts for RTT symptoms and that postnatal restoration of MeCP2 deficiency in the CNS, even after RTT onset, can lead to the reversal of neurological symptoms. These findings have led to the notion that RTT rescue may be achieved by pharmacological treatment that may induce MeCP2 up-regulation in MeCP2 deficient neurons, nonetheless considering the importance of correct MeCP2 dosage.

Significant proportion (up to 40%) of the classical RTT is caused by MECP2 nonsense mutations, leading to premature translational termination and truncated protein products. Studies using recombinant MeCP2 constructs harboring the most common RTT nonsense mutations, R168X, R255X, R270X and R294X, showed that gentamicin and geneticin can recover MeCP2 read-through efficiency up to 10-22% depending on the nucleotide context of a nonsense mutation [Brendel et al. (2009) Pediatr Res 65:520-523; Brendel et al., J Mol Med (2011) 89:389-398]. In addition, the recovered MeCP2 protein was traced to the cell nucleus suggesting that gentamicin does not interfere with its nuclear localization.

However, clinical applicability of aminoglycosides of the gentamicin family has been compromised by parallel findings of significant toxicity associated with its long-term administration and with reduced suppression efficiency at subtoxic doses [Kerem E (2004) Curr Opin Pulm Med 10: 547-552], in addition to its limited permeability through the blood-brain-barrier [Keeling K M, Bedwell D M (2005) Current Pharmacogenomics 3:259-269].

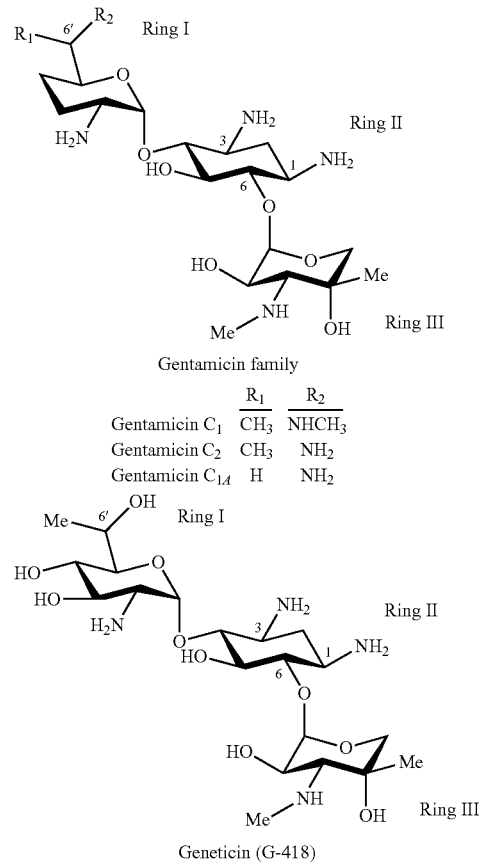

Some recently developed synthetic aminoglycosides have demonstrated significantly improved effects compared to gentamicin, evident in substantially higher suppression in RTT model and reduced acute toxicity in vitro [Kandasamy et al. J Med Chem 2012; 55:10630-43; Vecsler et al. PLoS One 2011; 6:e20733].

WO 2007/113841, by some of the present inventors, which is incorporated by reference as if fully set forth herein, teaches a class of paromomycin-derived aminoglycosides, which were designed specifically to exhibit high premature stop-codon mutations readthrough activity while exerting low cytotoxicity in mammalian cells and low antimicrobial activity, and can thus be used in the treatment of genetic diseases. This class of paromomycin-derived aminoglycosides was designed by introducing certain manipulations of a paromamine core, which lead to enhanced readthrough activity and reduced toxicity and antimicrobial activity. The manipulations were made on several positions of the paromamine core.

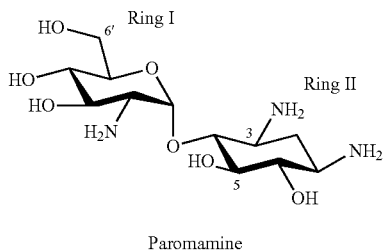

Paromamine

One such manipulation of the paromamine core which has been described in WO 2007/113841 is the determination of the beneficial role of a hydroxyl group at position 6' of the aminoglycoside core (see, for example, NB30 and NB54 below).

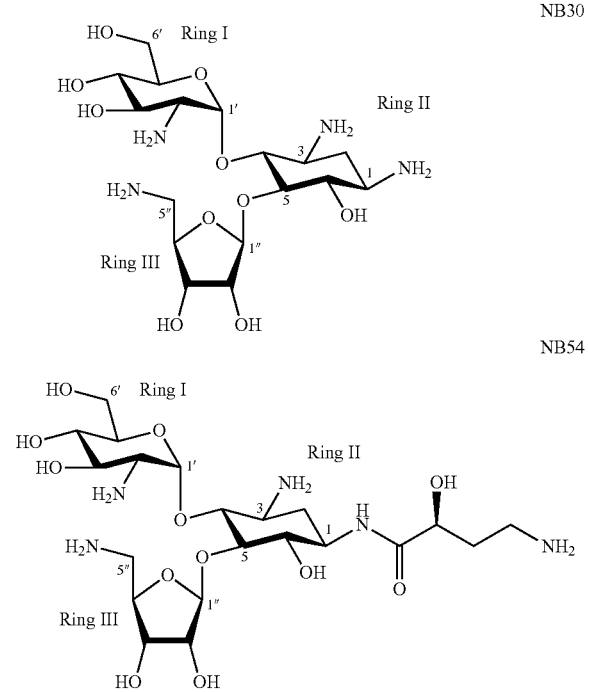

Another manipulation of the paromamine core which has been defined and demonstrated in WO 2007/113841 is the introduction of one or more monosaccharide moieties or an oligosaccharide moiety at position 3', 5 and/or 6 of the aminoglycoside core. This manipulation is reflected as "Ring III" in the exemplary compounds NB30 and NB54 shown hereinabove.

An additional manipulation of the paromamine core which has been defined and demonstrated in WO 2007/113841 is the introduction of an (S)-4-amino-2-hydroxybutyryl (AHB) moiety at position 1 of the paromamine core. This manipulation is reflected in exemplary compound NB54 shown hereinabove. It has been demonstrated that such an introduction of an AHB moiety provides for enhanced readthrough activity and reduced toxicity.

An additional manipulation of the paromamine core which has been described in WO 2007/113841 is the substitution of hydrogen at position 6' by an alkyl such as a methyl substituent. This manipulation has been exemplified in a derivative of compounds NB30 and NB54, referred to as NB74 and NB84 respectively.

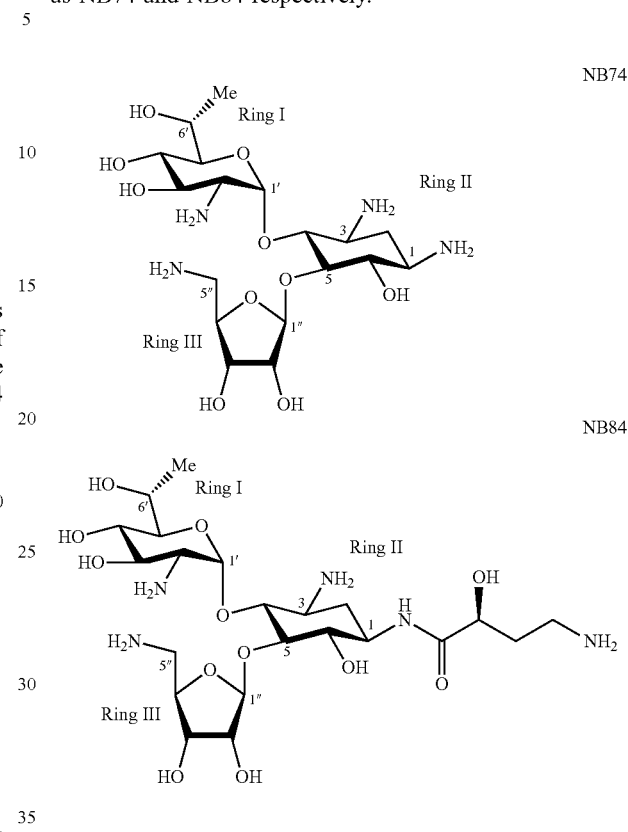

Vecsler et al. [(2011) PLoS ONE 6(6): e20733] have demonstrated that one of the compounds disclosed in WO 2007/113841 (NB54) induce dose-dependent suppression of MECP2 nonsense mutations more efficiently than gentamicin, which was evident at concentrations as low as 50 mg/ml. The read-through activity was mutation specific, with maximal full-length MeCP2 recovery in R168X (38%), R270X (27%) and R294X (18%). In addition, the recovered MeCP2 was translocated to the cell nucleus and led to parallel increase in one of the most important MeCP2 downstream effectors, the brain derived neurotrophic factor (BDNF).

Brendel et al (2011), supra, describe studies conducted in a mouse model carrying the R168X mutation in the MECP2 gene. Transfected HeLa cells expressing mutated MeCP2 fusion proteins and mouse ear fibroblasts isolated from the mouse model were treated with gentamicin and some of the aminoglycoside analogs described in WO 2007/113841 (NB30, NB54 and NB84). Readthrough of the R168X mutation in mouse ear fibroblasts using gentamicin was detected but at lower level than in HeLa cells, and the readthrough product, full-length Mecp2 protein, was located in the nucleus. NB54 and NB84 induced readthrough more effectively than gentamicin, with the readthrough of nonsense mutations achieved not only in transfected HeLa cells but also in fibroblasts of the generated Mecp2R168X mouse model.

International Patent Application Publication No. WO 2012/066546, by some of the present inventors, which is incorporated by reference as if fully set forth herein, teaches additional manipulations of the paromamine core, resulting in pseudo-trisaccharide aminoglycosides, characterized by a core structure based on Rings I, II and III of paromomycin with the addition of an alkyl in position 5" on Ring III. The chemical structures of exemplary aminoglycosides disclosed in WO 2012/066546 are presented in Background Art FIG. 1.

SUMMARY OF THE INVENTION

According to an aspect of some embodiments of the present invention there is provided a method of treating Rett syndrome in a subject in need thereof, the method comprising administering to the subject a therapeutically effective amount of a compound represented by formula I as described herein in any one of the respective embodiments.

According to an aspect of some embodiments of the present invention there is provided a compound represented by formula I, as described herein in any one of the respective embodiments, the compound being for use in the treatment of Rett syndrome in a subject in need thereof.

According to an aspect of some embodiments of the present invention, there is provided a use of a compound represented by formula I, as described herein in any one of the respective embodiments, in the manufacture of a medicament for the treatment of Rett syndrome in a subject in need thereof.

According to an aspect of some embodiments of the present invention there is provided a pharmaceutical composition comprising a compound represented by formula I, as described herein in any one of the respective embodiments, and a pharmaceutically acceptable carrier, the composition being packaged in a packaging material and identified in print, in or on the packaging material, for use in the treatment of Rett syndrome.

According to the present embodiments, the compound is represented by Formula I as follows:

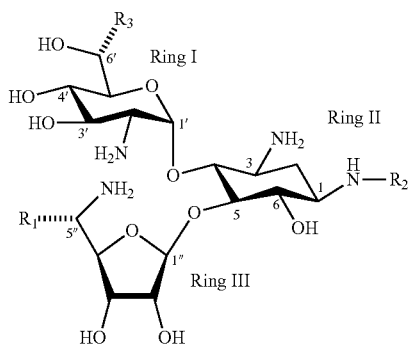

Formula I wherein:

$R_1$ is selected from the group consisting of alkyl, cycloalkyl and aryl;

$R_2$ is hydrogen or (S)-4-amino-2-hydroxybutyryl (AHB);

$R_3$ is selected from the group consisting of hydrogen, alkyl, cycloalkyl and aryl; and a stereo-configuration of each of position 6' and position 5" is independently an R configuration or an S configuration, or is a pharmaceutically acceptable salt thereof.

According to some of any of the embodiments described herein, $R_1$ is alkyl.

According to some of any of the embodiments described herein, the alkyl is methyl.

According to some of any of the embodiments described herein, $R_2$ and $R_3$ are each hydrogen.

According to some of any of the embodiments described herein, $R_2$ is AHB and $R_3$ is hydrogen.

According to some of any of the embodiments described herein, $R_2$ is hydrogen and $R_3$ is alkyl.

According to some of any of the embodiments described herein, $R_2$ is AHB and $R_3$ is alkyl.

According to some of any of the embodiments described herein, the alkyl is methyl.

According to some of any of the embodiments described herein, the compound is selected from the group consisting of compounds NB118, NB119, NB122, NB123, NB124, NB125, NB127 and NB128.

According to some of any of the embodiments described herein, the compound is selected from the group consisting of compounds NB122, NB123, NB124, NB127 and NB128.

According to some of any of the embodiments described herein, the compound is NB122.

According to some of any of the embodiments described herein, the compound is NB124.

According to some of any of the embodiments described herein, the compound is NB127.

According to some of any of the embodiments described herein, the Rett syndrome is associated with a MECP2 premature stop codon mutation.

According to some of any of the embodiments described herein, the mutation is a nonsense mutation.

According to some of any of the embodiments described herein, the MECP2 nonsense mutation is selected from the group consisting of R168X, R255X, R270X and R294X.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
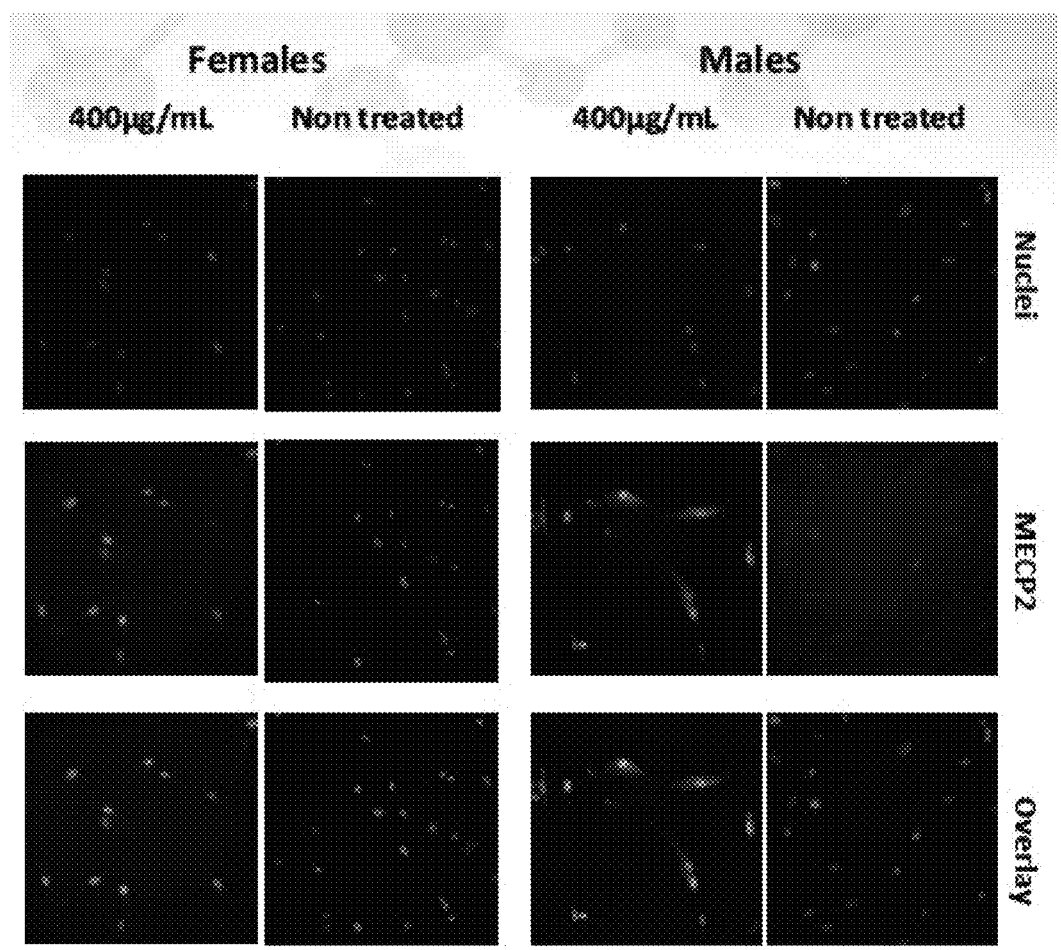

FIG. 1 presents high content screening automated microscope pictures obtained for fibroblasts derived from Human R294X Rett syndrome male and female patients, treated with 400 μg/mL for 3 days of NB124 compared with non-treated cells. Localization of MeCP2 protein was visualized by Molecular Device Imagexpress micro x1.

Figure 2A:
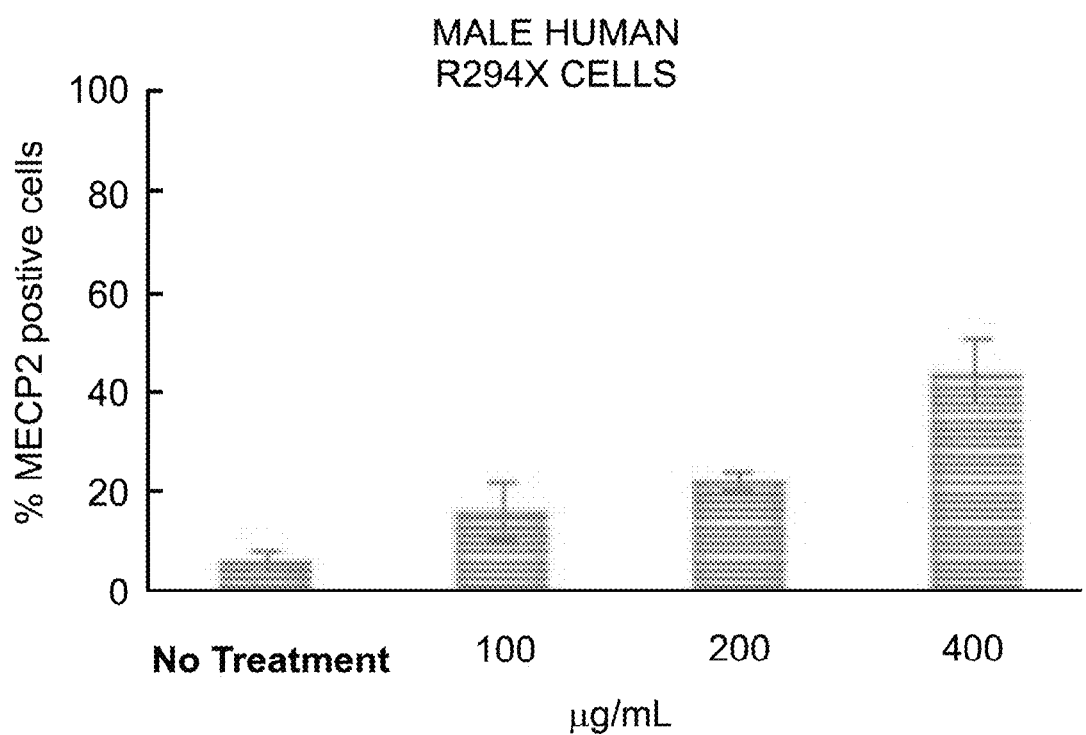
Figure 2B:
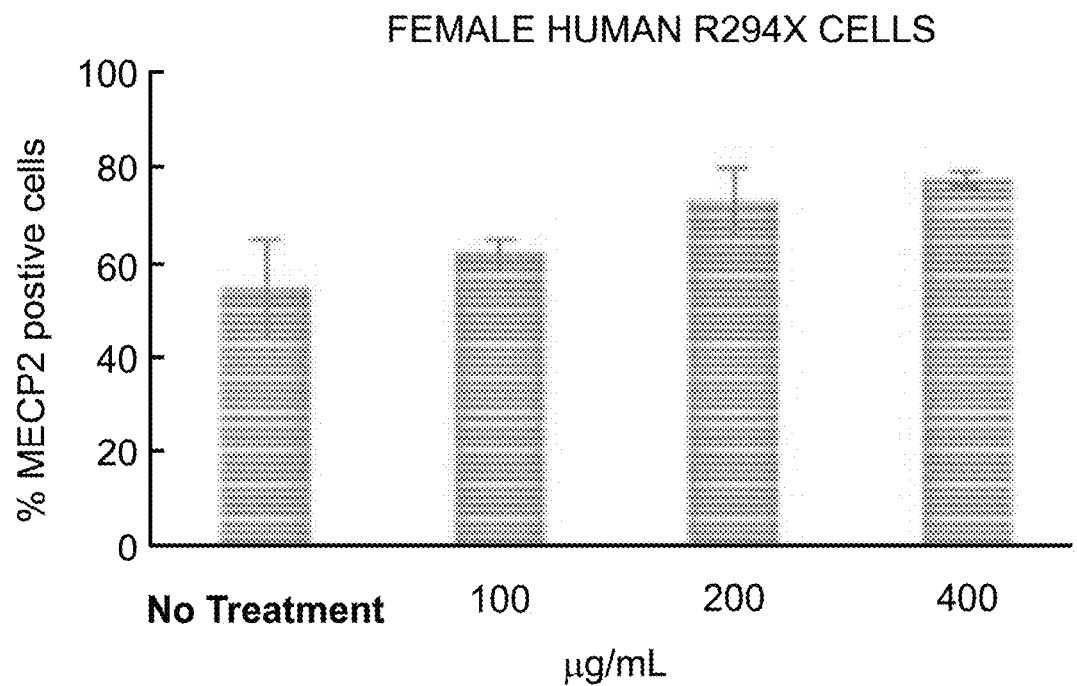

FIGS. 2A-2B are bar graphs presenting the number of MECP2 positive cells, in fibroblasts derived from Human R294X Rett syndrome male (FIG. 2A) and female (FIG. 2B)

patient, untreated, or treated with various concentrations of NB124, calculated using an automate algorithm.

Figure 3:
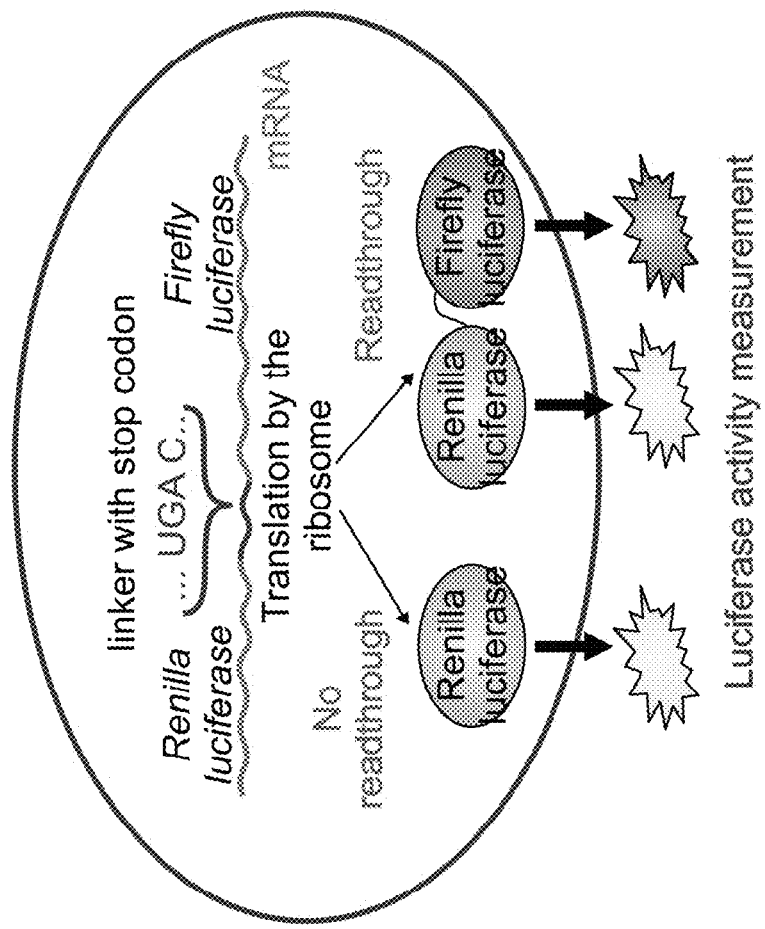
Figure 3:
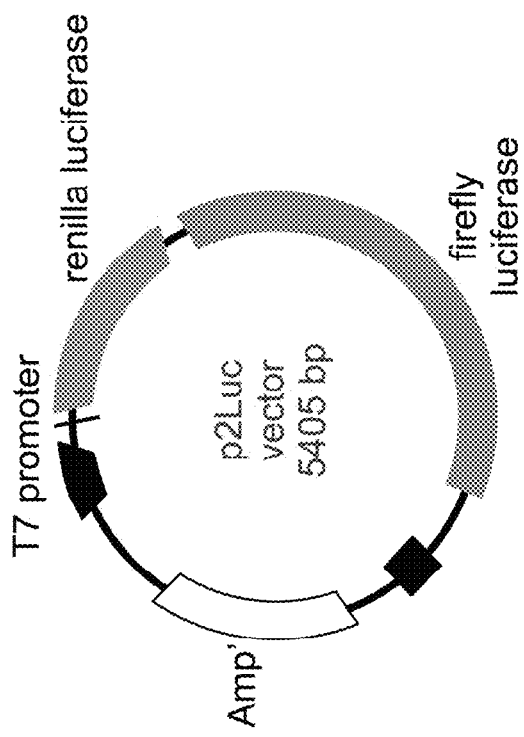

FIG. 3 presents an assay conducted with nucleic acid constructs featuring exemplary RTT nonsense mutations for determining readthrough activity of aminoglycosides.

Figure 4:
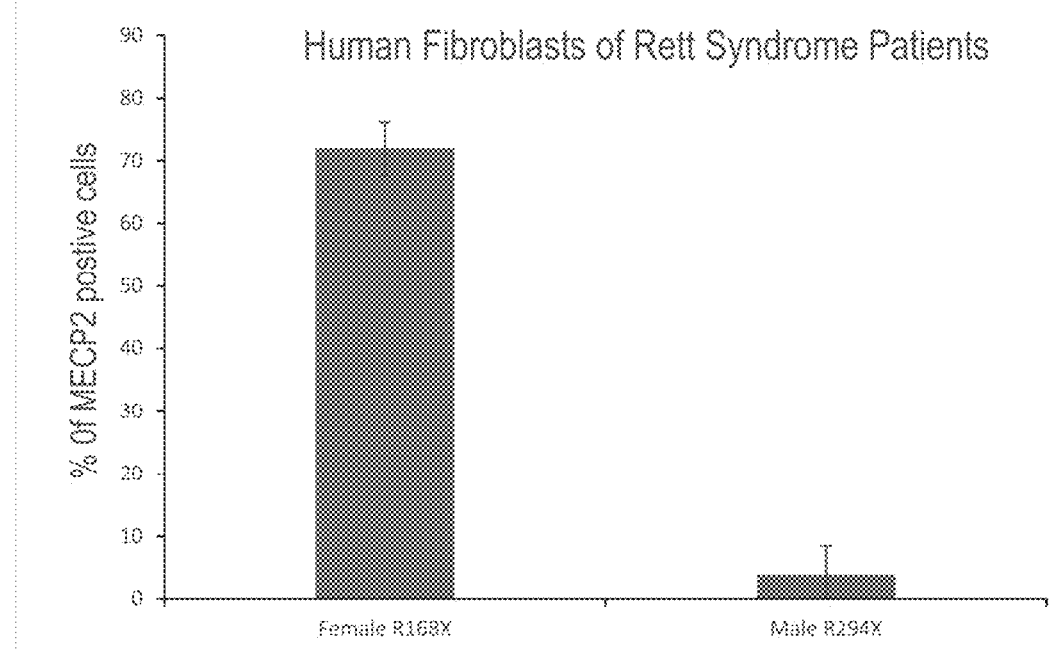

FIG. 4 is a bar graph showing the proportion of cells stained with MeCP2 at the cell nucleus out of all the DAPI-labeled cells used in the model described in Example 4.

Figure 5A:
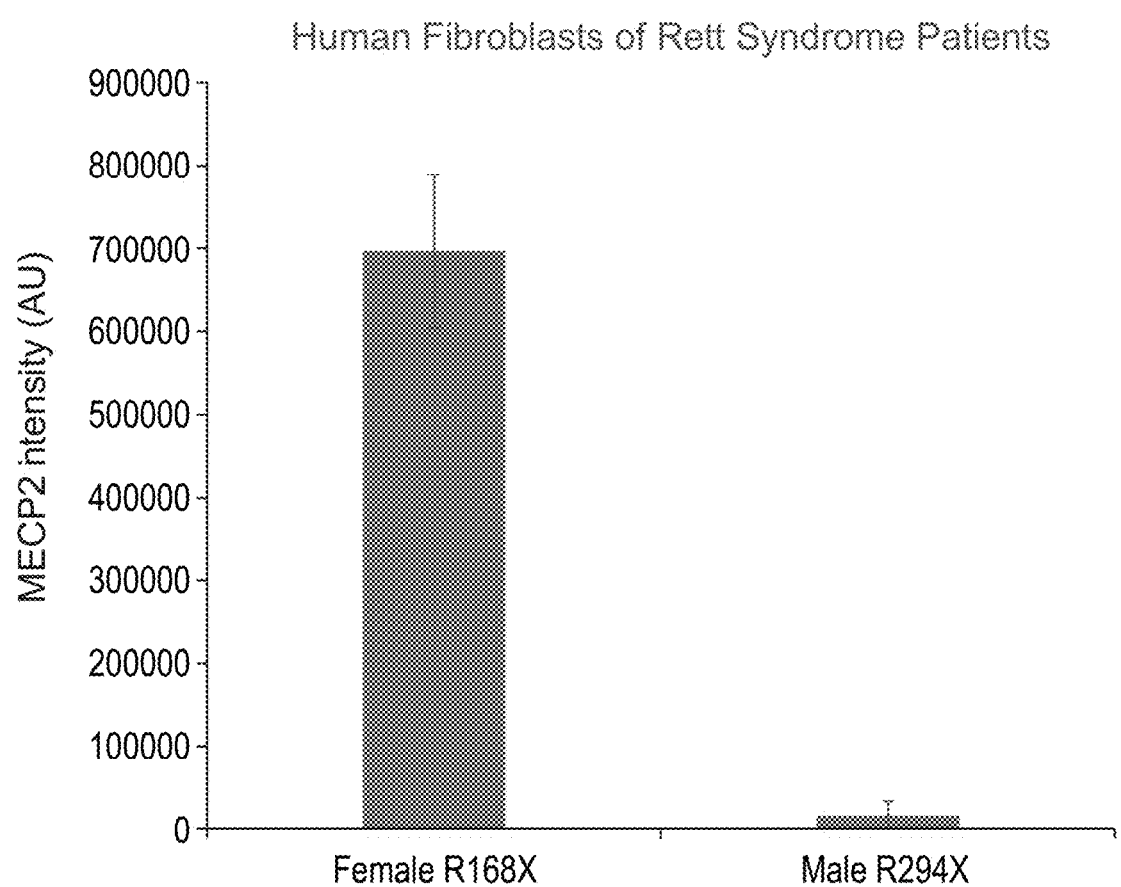
Figure 5B:
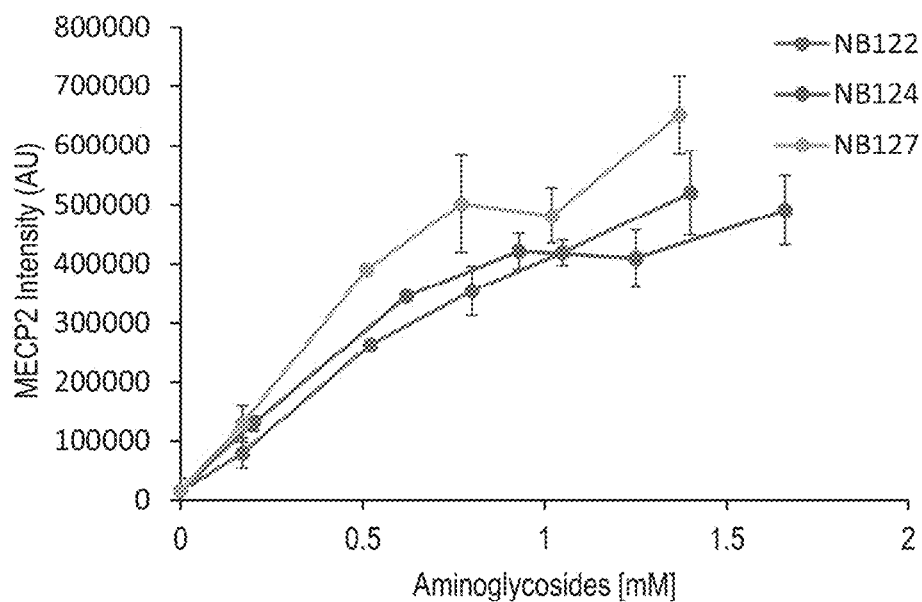
Figure 5C:
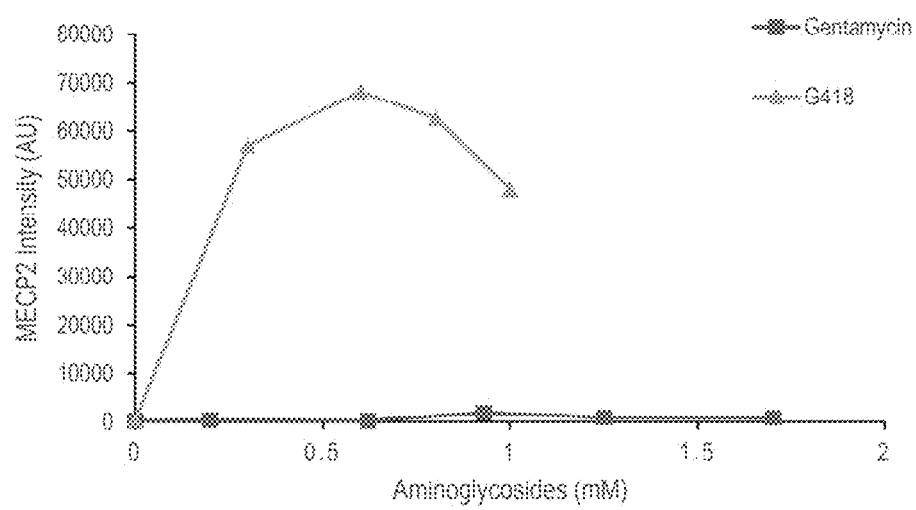

FIGS. 5A-5C are bar graphs showing MeCP2 expression level in the human fibroblasts of Rett Syndrome patients. Integrated MeCP2 staining intensities (2 areas) in the cell nucleus of human fibroblasts from Rett Syndrome patients after 3 days of non-treated R168X female and R294X male (FIG. 5A), none or 0.17-1.67 mM of NB122, NB124, NB127 treatment to R294X male (FIG. 5B), and none or 0.3-1 mM gentamicin or G418 treatment to R294X male (FIG. 5C). For the 0.5 mM dose of NB122, NB124, and NB127, only a single datum is considered.

Figure 6A:
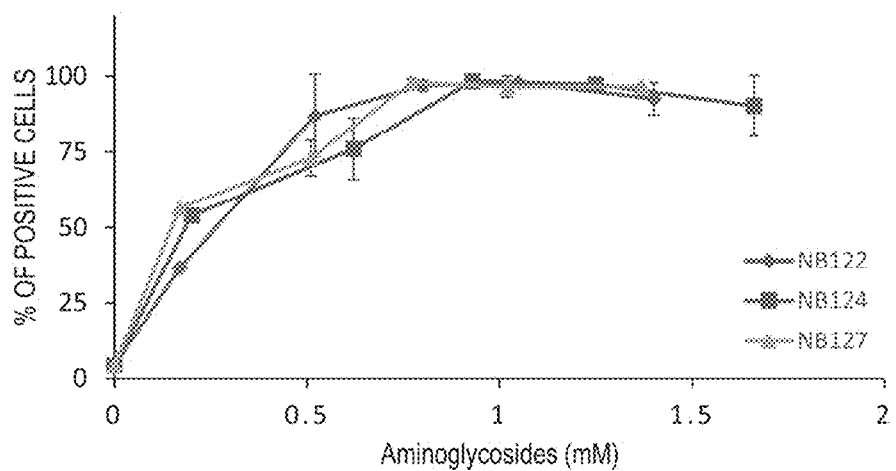
Figure 6B:
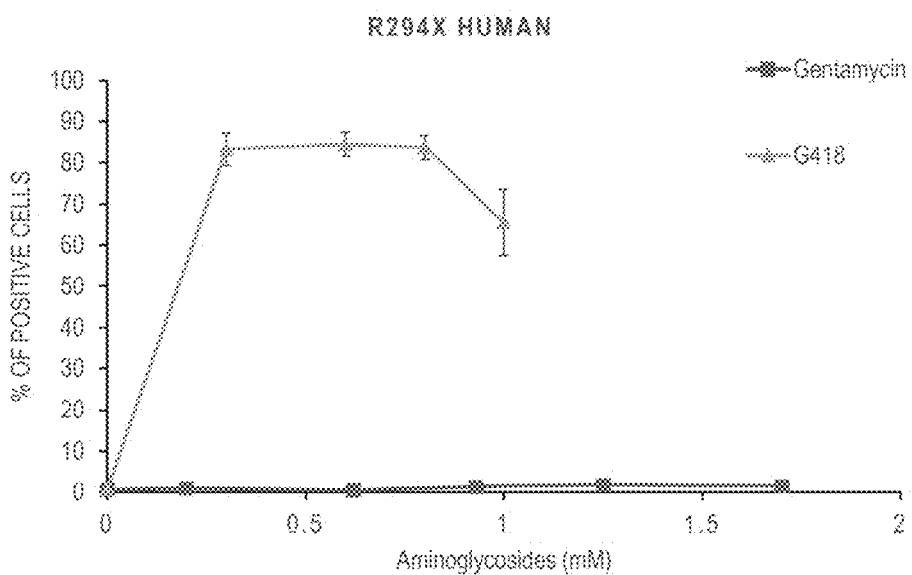

FIGS. 6A-6B present comparative plots showing the percent of MeCP2 stained cells in the human fibroblasts of male Rett Syndrome patient. Number of cells stained for MeCP2 in the cell nucleus of human fibroblasts from male Rett Syndrome patient bearing R294X mutation of the total positively stained cells for DAPI after 3 days of none or 0.17-1.67 mM of NB122, NB124, or NB127 treatment (FIG. 6A), and none or 0.3-1 mM gentamicin or G418 treatment (FIG. 6B). For the 0.5 mM dose of NB122, NB124, and NB127, only a single datum is considered.

Figure 7:
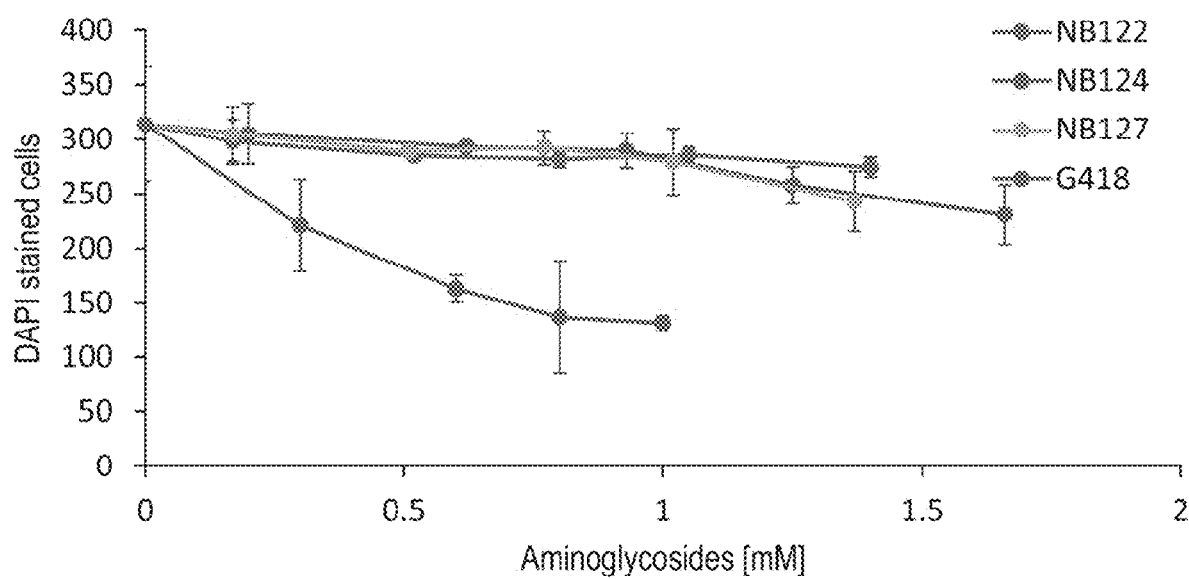

FIG. 7 presents comparative plots showing the number of positively stained cells for DAPI in the human fibroblasts of Rett Syndrome male patient after 3-days of treatment with NB122, NB124, NB127, or G418.

DESCRIPTION OF SPECIFIC EMBODIMENTS OF THE INVENTION

The present invention, in some embodiments thereof, relates to therapy and, more particularly, but not exclusively, to compositions and methods utilizing aminoglycoside analogs in the treatment of Rett syndrome.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have shown, in both in vitro and in vivo studies, and using transgenic mouse model and human fibroblast cells, that pseudo-trisaccharide aminoglycosides, characterized by a core structure based on Rings I, II and III of paromomycin with the addition of an alkyl in position 5" on Ring III, as disclosed in WO 2012/066546 and in any one of the respective embodiments herein, possess a high suppression activity of truncation mutations associated with Rett syndrome, namely high activity in inducing readthrough of a premature stop codon mutation associated with Rett syndrome.

As demonstrated in the Examples section that follows, the compounds presented herein were shown to possess a truncation mutation suppression activity, namely the ability to induce readthrough of various exemplary premature stop codon mutations associated with Rett syndrome. Such an activity renders these compounds highly suitable for use as therapeutically active agents for the treatment of Rett syndrome, for example, Rett syndrome characterized by a truncation mutation (premature stop codon mutation), e.g., a nonsense truncation mutation.

Thus, according to an aspect of the present invention there is provided a method of treating Rett syndrome in a subject in need thereof. The method, according to this aspect of the present invention, is effected by administering to the subject a therapeutically effective amount of one or more of the compounds represented herein by Formula I, including any one of the embodiments thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

According to an aspect of some embodiments of the present invention there is provided a compound represented by formula I as described in any one of the embodiments thereof, for use in the treatment of Rett syndrome in a subject in need thereof.

According to an aspect of some embodiments of the present invention there is provided a use of a compound represented by formula I, as described in any one of the embodiments thereof, in the manufacture of a medicament for the treatment of Rett syndrome in a subject in need thereof.

According to an aspect of some embodiments of the present invention, there is provided a pharmaceutical composition, comprising a pharmaceutically acceptable carrier and a compound represented by Formula I, as described in any one of the embodiments thereof, the composition being identified for use in the treatment of Rett syndrome in a subject in need thereof.

In any one of the present embodiments, the phrase "Rett syndrome", is used herein interchangeably with the expressions RTT and MIM 312750, and describes an X-linked postnatal neurodevelopmental disorder widely known in the art. Rett syndrome is typically diagnosed upon appearance of symptoms well recognized in the art (some of which are listed in the Background section hereinabove), which may optionally be supported by laboratory test to confirm the presence (and/or type) of the genetic mutation causing the disorder. Encompassed herein are typical, atypical and congenital Rett syndrome.

In some embodiments of the present invention, a typical Rett syndrome is associated with a mutation in the methyl CpG binding protein 2, or MECP2, gene, which encodes methyl-CpG-binding protein-2, MeCP2. MECP2 gene is found near the end of the long arm of the X chromosome at Xq28.

An exemplary atypical form of RTT, which is characterized by infantile spasms or early onset epilepsy, is assumed to be caused by a mutation to the gene encoding cyclin-dependent kinase-like 5 (CDKL5).

In some embodiments, for any of the mutations described herein, the mutation is a de novo mutation, which is not inherited, and in which the subject's parents are generally genotypically normal, without a MECP2 mutation or any other mutation associated with Rett syndrome.

In other embodiments, for any of the mutations described herein, the mutation is inherited. In some of these embodiments, the mutation is derived from the male copy of the X chromosome. In some of these embodiments, the mutation is inherited from phenotypically normal mothers who have a germline mutation in the gene encoding MeCP2.

In some of any one of the embodiments described herein, the Rett syndrome is associated with a truncation mutation or premature stop codon mutation.

In some of any one of the embodiments described herein, the Rett syndrome is associated with a truncation mutation or premature stop codon mutation in the gene encoding MeCP2 (including both isoform thereof), which is also referred to herein as MECP2 premature stop codon mutation.

In some embodiments, the mutation, for example, the MECP2 premature stop codon mutation can be a missense mutation, a nonsense mutation or frame-shift mutation.

In some embodiments, the mutation, for example, the MECP2 premature stop codon mutation is a nonsense mutation.

In some of any one of the embodiments described herein, the Rett syndrome is associated with one or more of the MECP2 mutations known in the art (about 200 currently known).

In some embodiments, the Rett syndrome is associated with one or more of the MECP2 nonsense mutations: R168X, R255X, R270X and R294X, as these mutations are known in the art.

In any of the methods and uses described herein, the compounds described herein can be utilized either per se or form a part of a pharmaceutical composition, which further comprises a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglycoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran.

Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compound as presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation associated with Rett syndrome). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of Rett syndrome, according to any one of the embodiments described herein, and any combination thereof.

In any of the composition, methods and uses described herein, the compounds can be utilized in combination with other agents useful in the treatment of the genetic disorder.

Being primarily directed at treating a genetic disorder, which is chronic, the compounds presented herein or pharmaceutical compositions containing the same are expected to be administered throughout the lifetime of the subject being treated, or at least a substantial portion of the subject's lifetime. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation readthrough drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease, and may cause the emergence of resistance in some pathological strains of microorganisms.

In some embodiments, the compounds presented herein have substantially no antibacterial activity. By "no antibacterial activity" it is meant that the minimal inhibition concentration (MIC) thereof for a particular strain is much higher than the concentration of a compound that is considered an antibiotic with respect to this strain. Further, the MIC of these compounds is notably higher than the concentration required for exerting truncation mutation suppression activity.

Being substantially non-bactericidal, the compounds presented herein do not exert the aforementioned adverse effects and hence can be administered via absorption paths that may contain benign and/or beneficial microorganisms that are not targeted and thus their preservation may even be required. This characteristic of the compounds presented herein renders these compounds particularly effective drugs against Rett syndrome since they can be administered repetitively and during life time, without causing any antibacterial-related adverse, accumulating effects, and can further be administered orally or rectally, i.e. via the GI tract, which is a very helpful and important characteristic for a drug directed at treating chronic disorders.

In any one of the methods, uses and compositions described herein, including any one of the embodiments thereof, and any combination of these embodiments, the compound useful in the treatment of Rett syndrome is one or more of the compounds collectively represented by Formula I:

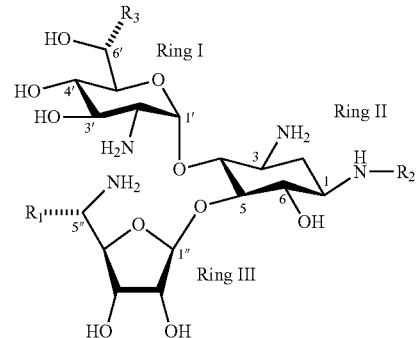

Formula I or a pharmaceutically acceptable salt thereof, wherein:

$R_1$ is selected from the group consisting of alkyl, cycloalkyl and aryl, and is preferably alkyl;

$R_2$ is hydrogen or (S)-4-amino-2-hydroxybutyryl (AHB), or an alternative to AHB, as described hereinbelow;

$R_3$ is selected from the group consisting of hydrogen, alkyl, cycloalkyl or aryl, and is preferably hydrogen or alkyl; and a stereo-configuration of each of position 6' and position 5" is independently an R configuration or an S configuration.

Embodiments of the present invention further encompass compounds featuring Rings I and II as in Formula I, in which Ring III as depicted in Formula I is at a position other than O5 on Ring II, for example, is at position O6 on Ring II and/or one or more of positions 3' and 4' on Ring I. In some of these embodiments, the compound is a trisaccharide, having Ring III as depicted herein attached to one position of Rings I or II.

The terms "hydroxyl" or "hydroxy", as used herein, refer to an —OH group.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low alkyl, having 1-4 carbon atoms (namely, methyl, ethyl, propyl and butyl).

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl.

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms. An alkyl can be substituted or unsubstituted. When substituted, the substituent can be, for example, an alkyl (forming a branched alkyl), an alkenyl, an alkynyl, a cycloalkyl, an aryl, a heteroaryl, a halo, a hydroxy, an alkoxy and a hydroxyalkyl as these terms are defined hereinbelow.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl cycloalkyl, alkenyl, alkynyl, aryl, heteroaryl and heteroalicyclic. Representative examples are morpholine, piperidine, piperazine, tetrahydrofurane, tetrahydropyrane and the like.

The term "halide", as used herein, refers to the anion of a halo atom, i.e. F—, Cl—, Br and I.

The term "halo" refers to F, Cl, Br and I atoms as substituents.

The term "alkoxy" refers to an R'—O" anion, wherein R' is as defined hereinabove.

The term "hydroxyalkyl," as used herein, refers to an alkyl group substituted with one hydroxy group, e.g., hydroxymethyl, p-phydroxyethyl and 4-hydroxypentyl.

The term "alkoxyalkyl," as used herein, refers to an alkyl group substituted with one alkoxy group, e.g., methoxymethyl, 2-methoxyethyl, 4-ethoxybutyl, n-propoxyethyl and t-butylethyl.

The moiety (S)-4-amino-2-hydroxybutyryl, is also referred to herein as AHB.

According to some embodiments of the present invention, an alternative to the AHB moiety can be the α-hydroxy-β-aminopropionyl (AHP) moiety. These so-called side chains or optional moieties are believed to block the access of aminoglycoside-modifying enzymes to the target sites. Moreover, AHB or AHP contain a 1,3- or 1,2-hydroxylamine moiety that binds to phosphodiesters and to the hoogsten base face of guanosine of the A-site of 16S rRNA. It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP. For example, 2-amino-3-hydroxybutyryl, 3-amino-2-hydroxypentanoyl, 5-amino-3-hydroxyhexanoyl and the likes.

Herein, it is to be understood that whenever reference is made to AHB, equivalent groups as described herein (e.g., AHP) are also encompassed.

As used herein, the phrase "moiety" describes a part, and preferably a major part, of a chemical entity, such as a molecule or a group, which has underwent a chemical reaction and is now covalently linked to another molecular entity. This term is used herein to define a radical of the indicated group, which substitutes a respective position of the skeleton of a compound.

According to some embodiments of the present invention, $R_1$ is alkyl.

According to some embodiments, $R_1$ is a lower alkyl as defined herein, including, but not limited to, methyl, ethyl, propyl, butyl, and isopropyl. According to some embodiments, $R_1$ is methyl.

Alternatively, $R_1$ is cycloalkyl, including, but not limited to, cyclopropyl, cyclobutyl, cyclopentyl and cyclohexyl.

Further alternatively, $R_1$ is aryl, such as substituted or unsubstituted phenyl. Non-limiting examples include phenyl and toluene.

In some embodiments of the present invention, $R_1$ is alkyl, as described herein, and $R_2$ and $R_3$ are each hydrogen.

Exemplary aminoglycoside compounds which exhibit hydrogen in positions $R_2$ and $R_3$ include:

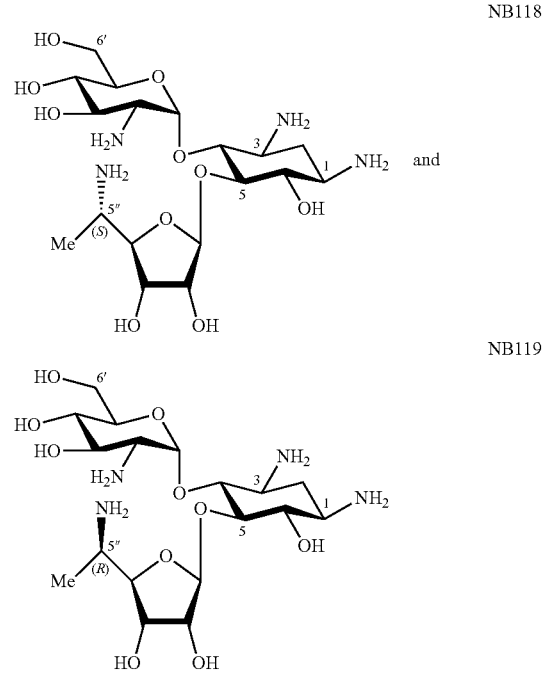

which differ from each other in the stereo-configuration of the chiral center at position 5" of Ring III.

Optionally, $R_1$ is cycloalkyl, as described herein, and $R_2$ and $R_3$ are each hydrogen. Such compounds can have as R or S stereo-configuration of the chiral center at position 5" of Ring III.

Optionally, $R_1$ is aryl, as described herein, and $R_2$ and $R_3$ are each hydrogen. Such compounds can have as R or S stereo-configuration of the chiral center at position 5" of Ring III.

In some embodiments of the present invention, $R_1$ is alkyl, as described herein, $R_2$ is AHB and $R_3$ is a hydrogen atom.

Exemplary aminoglycoside compounds having an AHB moiety at position $R_2$ and hydrogen in $R_3$ include:

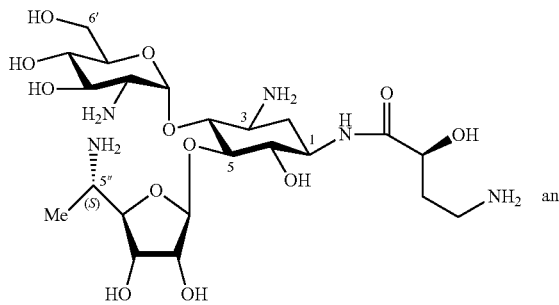

NB122

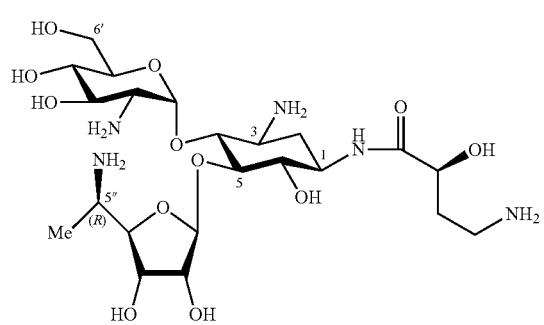

NB123 which differ from each other in the stereo-configuration of the chiral center at position 5" of Ring III.

Optionally, $R_1$ is cycloalkyl, as described herein, $R_2$ is AHB and $R_3$ is a hydrogen atom. Such compounds can have as R or S stereo-configuration of the chiral center at position 5" of Ring III.

Optionally, $R_1$ is aryl, as described herein, $R_2$ is AHB and $R_3$ is a hydrogen atom. Such compounds can have as R or S stereo-configuration of the chiral center at position 5" of Ring III.

In some embodiments of the present invention, $R_1$ is alkyl, as described herein, $R_2$ is hydrogen and $R_3$ is alkyl. Such compounds can have as R or S stereo-configuration of the chiral center at position 5" of Ring III.

Optionally, $R_1$ is cycloalkyl, as described herein, $R_2$ is hydrogen and $R_3$ is alkyl. Such compounds can have as R or S stereo-configuration of the chiral center at position 5" of Ring III.

Optionally, $R_1$ is aryl, as described herein, $R_2$ is hydrogen and $R_3$ is alkyl. Such compounds can have as R or S stereo-configuration of the chiral center at position 5" of Ring III.

According to some embodiments of the present invention, in any of the above-described embodiments where $R_3$ is alkyl, $R_3$ is a lower alkyl, as defined herein. According to these embodiments, $R_3$ is methyl.

Optionally, $R_1$ is alkyl, as described herein, $R_2$ is hydrogen and $R_3$ is cycloalkyl. Such compounds can have as R or S stereo-configuration of the chiral center at position 5" of Ring III.

Optionally, $R_1$ is cycloalkyl, as described herein, $R_2$ is hydrogen and $R_3$ is cycloalkyl. Such compounds can have as R or S stereo-configuration of the chiral center at position 5" of Ring III.

Optionally, $R_1$ is aryl, as described herein, $R_2$ is hydrogen and $R_3$ is cycloalkyl. Such compounds can have as R or S stereo-configuration of the chiral center at position 5" of Ring III.

Optionally, $R_1$ is alkyl, as described herein, $R_2$ is hydrogen and $R_3$ is aryl. Such compounds can have as R or S stereo-configuration of the chiral center at position 5" of Ring III.

Optionally, $R_1$ is cycloalkyl, as described herein, $R_2$ is hydrogen and $R_3$ is aryl. Such compounds can have as R or S stereo-configuration of the chiral center at position 5" of Ring III.

Optionally, $R_1$ is aryl, as described herein, $R_2$ is hydrogen and $R_3$ is aryl. Such compounds can have as R or S stereo-configuration of the chiral center at position 5" of Ring III.

Exemplary aminoglycoside compounds which exhibit hydrogen in position $R_2$ and alkyl in position $R_3$ include:

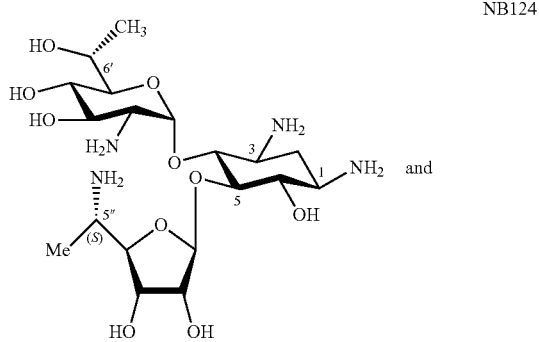

NB124

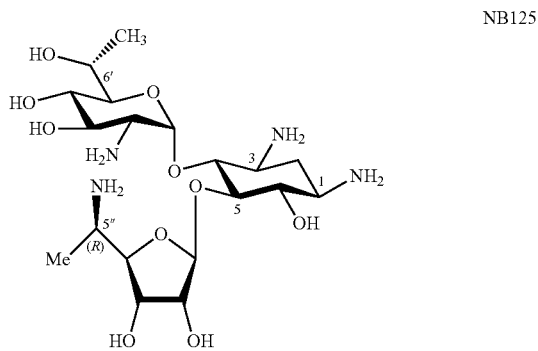

NB125 which differ from each other in the stereo-configuration of the chiral center at position 5" of Ring III.

In some embodiments of the present invention, $R_2$ is AHB and $R_3$ is alkyl. Exemplary aminoglycoside compounds wherein $R_2$ is AHB and $R_3$ is alkyl include:

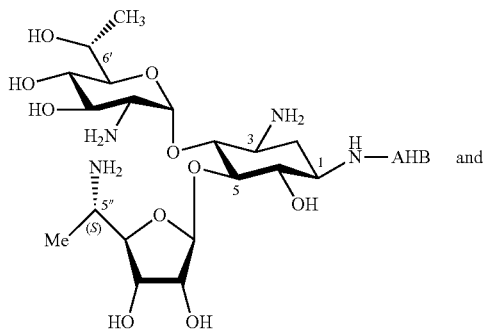

NB127

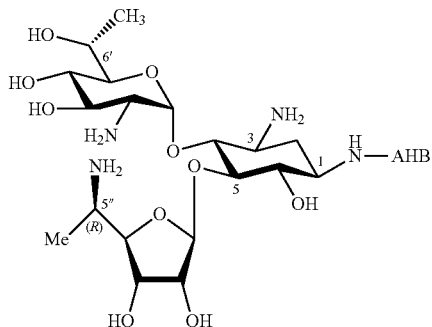

NB128 which differ from each other in the stereo-configuration of the chiral center at position 5" of Ring III.

Optionally, $R_1$ is cycloalkyl, as described herein, $R_2$ is AHB and $R_3$ is alkyl. Such compounds can have as R or S stereo-configuration of the chiral center at position 5" of Ring III.

Optionally, $R_1$ is aryl, as described herein, $R_2$ is AHB and $R_3$ is alkyl. Such compounds can have as R or S stereo-configuration of the chiral center at position 5" of Ring III.

According to some embodiments of the present invention, in any of the above-described embodiments where $R_3$ is alkyl, $R_3$ is a lower alkyl, as defined herein. According to these embodiments, $R_3$ is methyl.

Optionally, $R_1$ is alkyl, as described herein, $R_2$ is AHB and $R_3$ is cycloalkyl. Such compounds can have as R or S stereo-configuration of the chiral center at position 5" of Ring III.

Optionally, $R_1$ is cycloalkyl, as described herein, $R_2$ is AHB and $R_3$ is cycloalkyl. Such compounds can have as R or S stereo-configuration of the chiral center at position 5" of Ring III.

Optionally, $R_1$ is aryl, as described herein, $R_2$ is AHB and $R_3$ is cycloalkyl. Such compounds can have as R or S stereo-configuration of the chiral center at position 5" of Ring III.

Optionally, $R_1$ is alkyl, as described herein, $R_2$ is AHB and $R_3$ is aryl. Such compounds can have as R or S stereo-configuration of the chiral center at position 5" of Ring III.

Optionally, $R_1$ is cycloalkyl, as described herein, $R_2$ is AHB and $R_3$ is aryl. Such compounds can have as R or S stereo-configuration of the chiral center at position 5" of Ring III.

Optionally, $R_1$ is aryl, as described herein, $R_2$ is AHB and $R_3$ is aryl. Such compounds can have as R or S stereo-configuration of the chiral center at position 5" of Ring III.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a hydroxyl anion (O) and a cation such as, but not limited to, ammonium, sodium, potassium and the like. Another example, without limitation, of a pharmaceutically acceptable salt would be an ammonium cation and an acid addition salt thereof. Examples of acid addition salts include, but are not limited to, hydrochloric acid addition salt, sulfuric acid addition salt (sulfate salt), acetic acid addition salt, ascorbic acid addition salt, benzenesulfonic acid addition salt, camphorsulfonic acid addition salt, citric acid addition salt, maleic acid addition salt, methanesulfonic acid addition salt, naphthalenesulfonic acid addition salt, oxalic acid addition salt, phosphoric acid addition salt, succinic acid addition salt, sulfuric acid addition salt, tartaric acid addition salt, and toluenesulfonic acid addition salt.

According to some embodiments of the present invention, the acid addition salt is a sulfate salt.

According to some embodiments, the compounds presented herein are selective towards the eukaryotic cellular translation system versus that of prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the ribosome is involved in translating a gene, have a higher affinity to the eukaryotic ribosomal A-site, or otherwise are selective towards the eukaryotic A-site, versus the prokaryotic ribosomal A-site, as well as the mitochondrial ribosomal A-site which resembles its prokaryotic counterpart.

In some embodiments of the present invention, the compounds described herein include any one of the compounds disclosed in WO 2012/066546.

Any one of the compounds described herein can be prepared using the processes described in WO 2012/066546.

It is expected that during the life of a patent maturing from this application many relevant mutations associated with Rett syndrome, particularly premature stop codon mutations, will be uncovered and the scope of the expression Rett syndrome is intended to include all such mutations a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Exemplary compounds, according to some embodiments of the present invention, referred to herein as NB118, NB119, NB122, NB123, NB124, NB125, NBI26, NB127 and NB128, were prepared, as sulfate salts, as described in WO 2012/066546.

All other reagents were obtained from known vendors, unless otherwise indicated.

Primary antibody against the C-terminal of MeCP2 was obtained from Cell signaling.

Fibroblasts derived from Human R294X Rett syndrome male and female patients were obtained from Prof Bruria Ben Zeev, Edmond and Lilly Safra Pediatric Hospital, Sheba Medical Center, Tel Hashomer, Israel.

Nucleic acid constructs harboring Rett R168X, R270X, and R294X mutations were obtained from ProGen Protein & Gene Engineering, Israel.

High content screening assay was performed using a microscope and ImageXpress Micro XL (Molecular Devices, Sunnyvale, Calif.), while employing MetaXpress 2.0 software (Molecular Devices).

Dual luciferase reporter assay system was obtained from Promega.

HEK-293 (human embryonic kidney) cells were obtained from ATCC.

Example 1

MECP2 Readthrough in Rett Human R294X Cells

Fibroblasts derived from Human R294X Rett syndrome male and female patients were plated in a 384 black clear bottom plate at 750 cells/well, Cells were treated with 100, 200 and 400 µg/mL of NB124 for 3 days. Localization of endogenous MeCP2 protein was visualized by using a specific MeCP2 antibody detecting the C-terminal part of the protein and immunofluorescent microscopy.

FIG. 1 presents high content screening automated microscope pictures obtained for cells treated with 400 µg/mL of NB124 compared with non-treated cells, and show MECP2 nuclei localization and translation in all tested samples, and enhanced MECP2 translation in the treated samples.

The localization of MECP2 in the nuclai of the cell indicates that the protein retained is functionality and was able to return from the plasma to the nuclai.

The number of MECP2 positive cells was calculated using an automate algorithm and the obtained data is presented in FIGS. 2A-2B. As shown therein, in both male and female cells, the MECP2 was translated in dose dependent manner: 40% of male cells, treated with NB124 at 400 µg/mL were found positive for MECP2 following treatment; and over 60% of female cells, treated with NB124 at 200 µg/mL or 400 µg/mL were found positive for MECP2 following treatment.

Example 2

In Vitro Studies of Readthrough Efficacy

Readthrough activity was assayed using TNT reticulocyte lysate (in-vitro), and the nucleic acid constructs: Rett R168X. R270X & R294X for the nonsense mutations tested, as depicted in FIG. 3.

The obtained plasmids in the presence of 0-50 µM of the tested aminoglycoside transcribed and translated using the TNT reticulocyte lysate quick-coupled transcription/translation system. Luciferase activity was determined 90 minutes post incubation at 30° C., using Dual luciferase reporter assay system, and read-through was calculated as shown in the follow equation:

$$\% \text{ Readthrough} = \frac{\frac{\text{Luminescence}(FF_{mut})}{\text{Luminescence}(Renilla_{wt})}}{\frac{\text{Luminescence}(FF_{wt})}{\text{Luminescence}(Renilla_{wt})}}$$

The obtained data is presented in Table I below.

In additional in vitro assays, the system described hereinabove was tested for various aminoglycosides, while using the above-described plasmids in the presence of 1.4 µM of the tested aminoglycoside, and calculating the readthrough activity according to the above-presented equation.

The values obtained for the readthrough activity (RT %) are presented in Table 2 below.

TABLE 2

|         | R168X | R270X | R294X |
|---------|-------|-------|-------|
| Control | 0.07  | 0.11  | 0.08  |
| NB122   | 2.45  | 5.12  | 2.97  |
| NB127   | 3.32  | 6.74  | 4.62  |

Example 3

Ex-Vivo Readthrough Efficacy and Toxicity Assays

Nucleic acid constructs harboring Rett R168X, R270X, and R294X mutations were inserted into HEK-293 (human embryonic kidney) cells using Calcium Phosphate method. Six hours post-transfection, the tested aminoglycosides, at a concentration of 0.3 or 1 mM were added. The cells were harvested following 16 hours incubation with the tested aminoglycoside using passive lysis buffer. Readthrough activity was calculated as described hereinabove (see, Example 2).

For the cytotoxicity assays, HEK-293 cells were grown in 96-well plates, the tested synthetic aminoglycosides, at various concentrations, were thereafter added (10 µL per well), and the cells were incubated for additional 24 hours. A cell proliferation assay (wst-1 based colorimetric assay), was performed by using 3-hour incubation. Optical density was measured using an ELISA plate reader.

The obtained data are presented in Table 3 (readthrough activity) and Table 4 (toxicity).

As shown therein, the aminoglycosides of embodiments of the present invention exhibit at least comparable if not improved readthrough efficacy, yet substantially lower toxicity compared with G418.

TABLE 1

| Compound[1] | IC50 [µm][2,3] | | | Translational Inhibition (TI) [µm][2,3] | | | TI/IC50[3] | | | RT %[4] |
|---|---|---|---|---|---|---|---|---|---|---|
| | R168X | R270X | R294X | R168X | R270X | R294X | R168X | R270X | R294X | |
| NB122 | 0.40 | 0.16 | 0.22 | 4.10 | 3.75 | 5.02 | 10 | 23 | 23 | 5.3% |
| NB123 | 1.66 | 1.39 | 1.75 | 22.23 | 14.48 | 60.84 | 13 | 10 | 35 | 3.8% |
| NB124 | 0.88 | 0.43 | 0.76 | 6.67 | 5.32 | 5.65 | 8 | 12 | 7 | 3.2% |
| NB127 | 0.19 | 0.46 | 0.25 | 2.44 | 2.27 | 2.25 | 13 | 5 | 9 | 4.0% |
| NB128 | <0.5 | <0.5 | 0.21 | 1.68 | 1.48 | 1.91 | NA | NA | 9 | 3.7% |

[1]Compounds were tested at 0-50 µM;
[2]IC50 and translational inhibition were calculated for a dose-escalating study;
[3]Constructs: Rett R168X, R270X, and R294X nonsense mutations tested.
[4]Readthrough (RT) activity assayed using TNT reticulocyte lysate (in-vitro); Maximal readthrough compared with wild type, below the TI concentration, calculated as described hereinabove.

TABLE 3

| Compounds/% Readthrough | | R168X | R270X | R294X |
|---|---|---|---|---|
| control | | 0.26 | 1.26 | 0.20 |
| G418 | 0.3 mM | 0.82 | 2.53 | 0.83 |
| | 1 mM | 1.37 | 3.34 | 1.03 |
| NB118 | 0.3 mM | 0.53 | 1.15 | 0.24 |
| | 1 mM | 0.62 | 1.45 | 0.29 |
| NB119 | 0.3 mM | 0.79 | 1.70 | 0.36 |
| | 1 mM | 0.81 | 1.75 | 0.39 |
| NB122 | 0.3 mM | 0.57 | 2.33 | 1.42 |
| | 1 mM | 2.43 | 4.33 | 2.30 |
| NB123 | 0.3 mM | 0.84 | 1.90 | 0.72 |
| | 1 mM | 1.84 | 3.67 | 1.58 |
| NB124 | 0.3 mM | 0.68 | 1.21 | 0.77 |
| | 1 mM | 1.01 | 2.37 | 1.26 |
| NB125 | 0.3 mM | 0.81 | 1.03 | 0.46 |
| | 1 mM | 0.62 | 1.61 | 0.57 |
| NB127 | 0.3 mM | 1.62 | 2.78 | 1.78 |
| | 1 mM | 3.23 | 5.49 | 2.67 |
| NB128 | 0.3 mM | 2.36 | 4.72 | 2.14 |
| | 1 mM | 3.52 | 5.64 | 2.84 |

TABLE 4

| | LC50 (mM) | |
|---|---|---|
| Compound | Mean | SD |
| Gentamicin | 4.0 | 0.6 |
| G418 | 2.1 | 0.2 |
| NB118 | 40.7 | 1.3 |
| NB119 | 32.2 | 0.9 |
| NB122 | 14.0 | 1.6 |
| NB123 | 19.1 | 2.9 |
| NB124 | 17.8 | 0.8 |
| NB125 | 26.6 | 5.9 |
| NB127 | 14.0 | 1.0 |

Example 4

In Vitro Studies of Readthrough Efficacy
(Escalating Doses)

A comparative study of readthrough effects of NB122, NB124, NB127 and the traditional aminoglycosides, gentamicin and G418 treatment, at escalating dose was conducted on human fibroblasts generated from Rett Syndrome patients bearing nonsense mutations. The full-length of MeCP2 translation and nuclei localization in these primary fibroblasts were analyzed using high content screening assay.

Materials and Method:

Fibroblasts were expanded from male Rett Syndrome patient (R294X) skin biopsies and cultured in Dulbecco's modified Eagle's medium (DMEM; Biological Industries, Israel) supplemented with 10% fetal calf serum (FCS), 2 mM L-glutamine, 100 mg/ml streptomycin and 100 units/ml penicillin (Biological Industries) at 37° C. in humidified incubator with 5% $CO_2$.

Human fibroblasts from female Rett Syndrome patient bearing R168X mutation were used as reference for MeCP2 expression, and were cultured under the same conditions and the male fibroblasts of R294X.

In Brief, 384-well black/transparent bottom plate was coated with poly-L-Lysine (Sigma; 1:5 in PBS) using 384-head offline Pintool system (GNF Systems, San Diego, Calif., USA; 30 ul/well). The poly-L-Lysine was aspirated after 30 minutes and dried for 20 minutes in the laminar hood. The human fibroblasts were thereafter plated at 700 cells per well using Multidrop 384 (Thermo Fisher Scientific, Waltham, Mass.) while mapping the plate.

G418 sulfate (Sigma), gentamicin sulfate (Sigma) or sulfate salts of NB122, NB124 and NB127 were daily added in quadruplicates into the plate medium for three days at escalating dose of 0 to 800 μg/mL.

At the end of the treatment, cells were fixed with 4% paraformaldehyde in PBS for 30 minutes using the robotic well-plate (Agilent Technologies, Santa Clara, Calif., USA) and automated liquid dispenser (EL406, BioTek). Permeabilization included incubation with 0.2% Triton X-100 in 2% BSA (Sigma) in PBS for 5 minutes followed by washing with 2% BSA in PBS for 5 minutes at room temperature.

The cells were then incubated overnight at 2-8° C. with primary antibody against the C-terminal of MeCP2 (Cell signaling) at 1:200 dilution in 0.2% Triton X-100, 2% BSA in PBS. On the following day, the cells were washed with PBS for three times using the robotic well-plate and the automated liquid dispenser.

Cells were then treated by a secondary antibody (Alexa Fluor® 488 Goat Anti-Rabbit; 1:1000) and 4,6-diamidino-2-phenylindole (DAPI; Sigma; 1:10000), diluted in 2% BSA in PBS for 1 hour and then washed four times with PBS using robotic well-plate and the automated liquid dispenser.

High content assay method was employed using microscope and ImageXpress Micro XL (Molecular Devices, Sunnyvale, Calif.) to acquire cell images, and image analysis was performed by using MetaXpress 2.0 software (Molecular Devices.

The following parameters were evaluated:

=Expression intensity of MECP2 in the nucleus: detection by immunostaining level with anti-MeCP2 c-terminal antibody, =Percent of positive cells: determined as the number of cells presenting MeCP2 expression in the nucleus is a fraction of the total number of cells stained by DAPI.

The aminoglycoside EC50 values in the aforementioned parameters were calculated using the GraphPad PRISM software (Graphpad Software) and nonlinear regression (one phase association) model.

Results:

Primary human fibroblasts of Rett Syndrome male patient harboring R294X mutation were treated with synthetic (NB122, NB124 and NB127) or natural (gentamicin and G418) aminoglycosides at increasing concentrations ranging from 100 to 800 μg/ml (0.17-1.67 mM) for 3 days. In addition, human fibroblasts of Rett Syndrome female patient bearing R168X mutation were cultured at the same plate, but were not treated. Expression levels of the full-length MeCP2 were evaluated using anti-MeCP2 C-terminal antibody. MeCP2 read-through efficiency was evaluated relative to the human female R168X mutant expressing the normal MeCP2 in 70% of cells (see, FIG. 4).

FIGS. 5A-5C show the extent of the full-length MeCP2 expression levels in fibroblasts from Rett Syndrome patients bearing R294X or R168X nonsense mutations. Non-treated fibroblasts from male R294X have shown only marginal expression level of MeCP2 protein in the nucleus, while the female R168X presented with substantial MeCP2 levels (FIG. 5A). Repeated dose for 3 days of NB122, NB124 and NB127 resulted with significant increase in the MeCP2 levels (FIG. 5B), demonstrating the MeCP2 readthrough efficacy of these synthetic aminoglycosides. There was substantial increase in MeCP2 staining after G418 administration, but only negligible amounts of MECP2 staining following gentamicin treatment (FIG. 5C).

The corresponding EC50 values of the readthrough efficacy, derived from the integrated MeCP2 staining intensities in the cell nucleus of human fibroblasts from male Rett Syndrome patient, were calculated and are presented in Table 5. These values show comparable readthrough efficacies of all the tested synthetic aminoglycosides (400-600 μM), whilst the EC50 for the G418 was shown to be fairly low (60 μM).

TABLE 5

| Compound | EC50 (μM) |
| --- | --- |
| NB122 | ~500* |
| NB124 | 417.9 |
| NB127 | 548.9 |
| Gentamicin | ** |
| G418 | 60.4 |

*The EC50 could not be calculated accurately, and thus estimated from the graph;
** The EC50 could not be calculated as there was limited effect of the aminoglycoside As shown in FIGS. 6A-6B, while immunofluorescence localization of the full-length MeCP2 with anti-MeCP2 C-terminal antibody in non-treated human fibroblasts from male Rett Syndrome (R294X) was measured to be 4% (see, FIG. 4), it has reached more than 90% of DAPI-stained cells following 3-days treatment with 0.8 mM or higher dose of NB122, NB124 and NB127 (FIG. 6A). Gentamicin treatment resulted with only very limited amounts of positively stained human fibroblasts from male Rett Syndrome for MECP2 (2%; FIG. 6B).

The calculated EC50 from the % of MeCP2 stained cells of the total positively stained cells for DAPI in human fibroblasts from male Rett Syndrome patient are presented in Table 6 and show somewhat comparable readthrough efficacies between synthetic aminoglycosides (higher than 400-600 μM).

TABLE 6

| Compound | EC50 (μM) |
| --- | --- |
| NB122 | 210.9 |
| NB124 | 193.5 |
| NB127 | 177.0 |
| G418 | * |
| Gentamicin | ** |

* The EC50 could not be calculated using the current model
** The EC50 could not be calculated as there was limited effect of the aminoglycoside As shown in FIGS. 5C and 6B, male Rett Syndrome patient fibroblasts treated for 3 days with G418 achieved plateau readthrough efficacy as well as 80%-100% MECP2 expression cells of the DAPI stained cells at the lowest treated dose group (0.15 mM). However, as shown in FIG. 7, a significant decrease of DAPI stained cells was also shown in this concentration. This decrease may be associated with G418 cell toxicity effect on these fibroblasts. Conversely, as further shown in FIG. 7, treatment with NB122, NB124 and NB127 for 3 days at up to a 10-fold dose (1.5 mM) was well tolerated.

In summary, this study has demonstrated that the effect of NB122, NB124, and NB127 on MeCP2 staining in male Rett Syndrome fibroblasts showed EC50 values lower than 200 μM, and that these treatments generated up to more than 90% positively stained MeCP2 cells of the DAPI-labeled cells (at a dose of 800 μM and up).

This study has further demonstrated that a daily gentamicin treatment (at up to 1.7 mM) for three days to male Rett Syndrome fibroblasts did not affect the MeCP2 expression.

Similar findings were previously published by Brendel et al. in J. Mol. Med. (Berl) (2011) 89:389-98, using similar experimental settings. The effect of the G418 treatment on the male Rett Syndrome fibroblasts was significant, with EC50 MeCP2 staining much lower than 300 μM and EC50 integrated MeCP2 staining intensities at 60 μM.

The safety margins for G418 using the presented Rett Syndrome model was calculated to be about 5-10-fold [EC50 at 60 μM and LC50 at 300-600 μM].

The safety margins of gentamicin in the described Rett Syndrome model could not be calculated as the efficacy was negligible. No significant cytotoxicity was documented in this study for gentamicin, which is in agreement with the LC50 of this aminoglycoside in HEK293 cells, presented in Example 3 hereinabove.

No significant cytotoxicity was documented herein for the tested NB122, NB124, and NB127.

The safety margins for the compounds described herein (e.g., NB122, NB124, and NB127) in terms of cell toxicity, using the presented Rett Syndrome model, the cytotoxicity determined by the aforementioned wst-1 study and the xCELLigence system ranges between 44-167-fold, suggesting higher safety margins compared to G418.

Example 5

Mouse Model for Rett Syndrome Patients with Nonsense Mutations

The compounds described herein are further tested in a MeCP2$^{R168X}$ knock-in mouse model for Rett Syndrome, as described, for example, in Wegener et al. [PLoS ONE 2014; 9(12): e115444]; or a MeCP2$^{R255X}$ knock-in mouse model as described, for example, in Pitcher et al., [Hum. Mol. Genet. 2015; 24(9):2662-72], or in a similar mouse model of Rett Syndrome with nonsense mutations. A compound as described herein is administered to the knock-in mice, parenterally, and the expression of full length MeCP2 from the corresponding mutated allele is determined. The animal life span and the animal model phenotype (e.g., impaired motor performance, incidence of arrhythmia, reduced activity, motor coordination dysfunction and decreased anxiety-like behavior, apneas and irregular breathing with reduced frequency, decreased motor performance) are positively affected.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of treating Rett syndrome in a subject in need thereof, the method comprising administering to the subject a therapeutically effective amount of a compound represented by formula I:

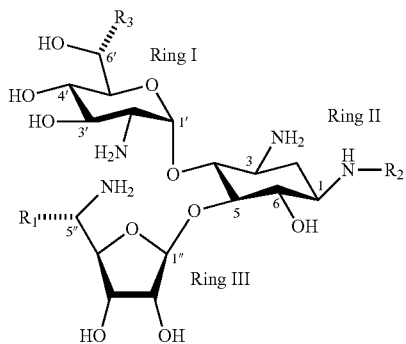

Formula I or a pharmaceutically acceptable salt thereof, wherein:
- $R_1$ is selected from the group consisting of alkyl, cycloalkyl and aryl;
- $R_2$ is hydrogen or (S)-4-amino-2-hydroxybutyryl (AHAB);
- $R_3$ is selected from the group consisting of hydrogen, alkyl, cycloalkyl and aryl;
- a stereo-configuration of position 5″ is an R configuration or an S configuration; and
- a stereo-configuration of position 6′, when chiral, is an R configuration or an S configuration.

2. The method of claim 1, wherein $R_1$ is alkyl.

3. The method of claim 2, wherein said alkyl is methyl.

4. The method of claim 1, wherein $R_2$ and $R_3$ are each hydrogen.

5. The method of claim 1, wherein $R_2$ is AHAB and $R_3$ is hydrogen.

6. The method of claim 1, wherein $R_2$ is hydrogen and $R_3$ is alkyl.

7. The method of claim 1, wherein $R_2$ is AHAB and $R_3$ is alkyl.

8. The method of claim 7, wherein said alkyl is methyl.

9. The method of claim 1, wherein the compound is selected from the group consisting of:

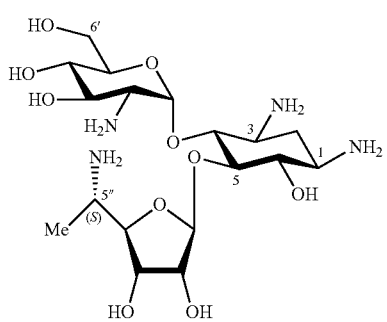
NB118

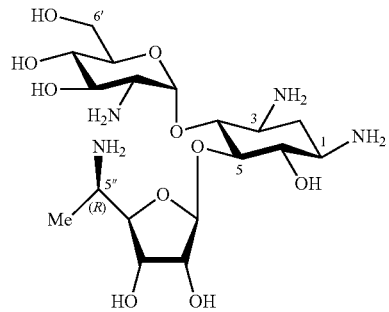
NB119

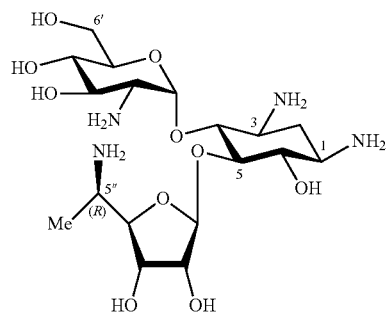
NB122

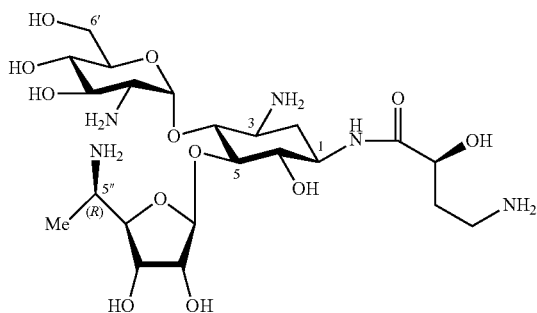
NB123

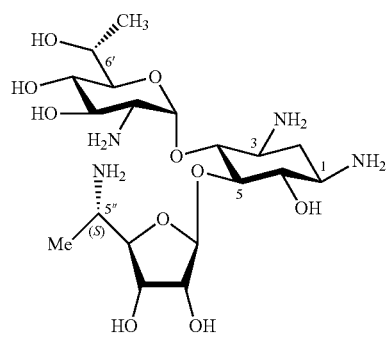
NB124

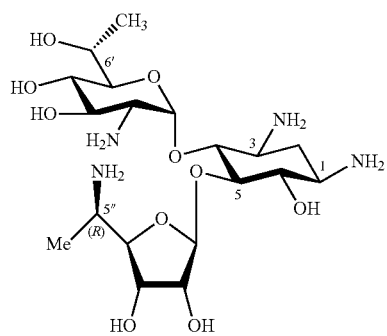
NB125
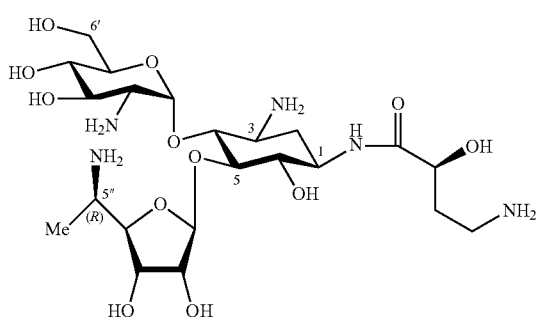
NB123
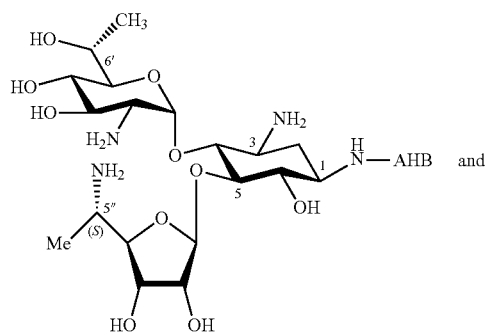
NB127
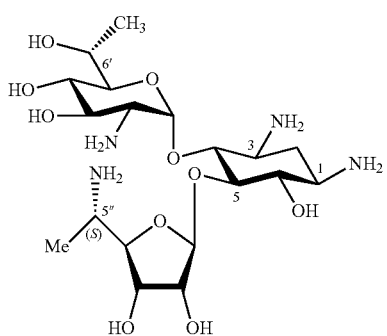
NB124
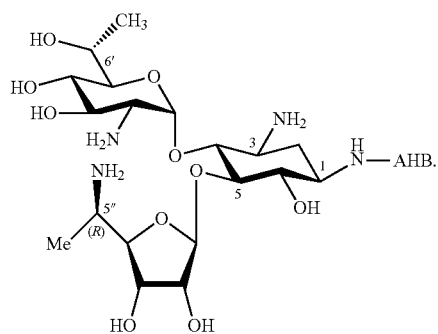
NB128
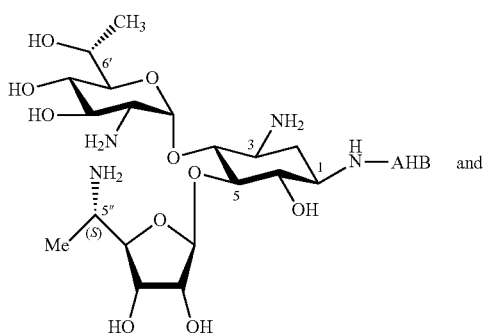
NB127 and
10. The method of claim 1, wherein the compound is selected from the group consisting of:
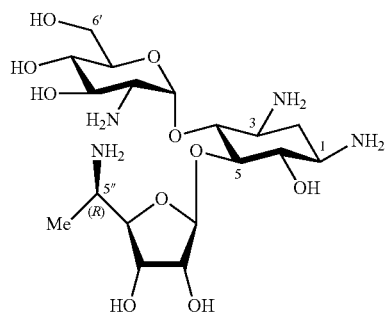
NB122
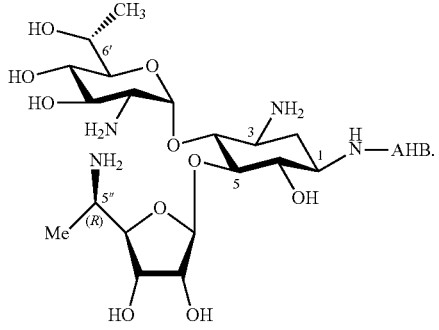
NB128

11. The method of claim 1, wherein the compound is

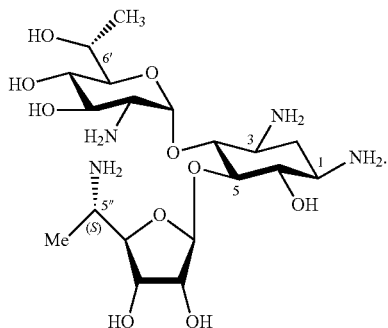

NB124

12. The method of claim 1, wherein said Rett syndrome is associated with a MECP2 premature stop codon mutation.

13. The method of claim 12, wherein said mutation is a nonsense mutation.

14. The method of claim 13, wherein said MECP2 nonsense mutation is selected from the group consisting of R168X, R255X, R270X and R294X.

15. A method of treating Rett syndrome in a subject in need thereof, the method comprising administering to the subject a therapeutically effective amount of a compound represented by formula I:

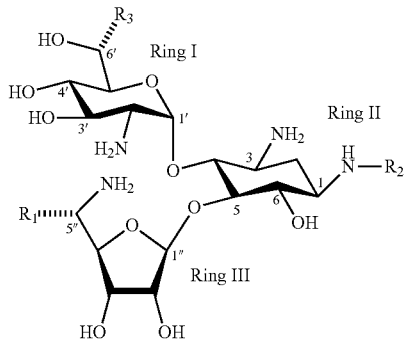

Formula I or a pharmaceutically acceptable salt thereof,
wherein:
$R_1$ is alkyl;
$R_2$ is hydrogen or (S)-4-amino-2-hydroxybutyryl (AHAB);
$R_3$ is alkyl;
a stereo-configuration of position 5" is an R configuration or an S configuration; and
a stereo-configuration of position 6', when chiral, is an R configuration or an S configuration.

16. The method of claim 15, wherein said alkyl is methyl.

17. The method of claim 15, wherein $R_2$ is hydrogen.

18. The method of claim 15, wherein $R_2$ is AHAB.

19. The method of claim 15, wherein said Rett syndrome is associated with a MECP2 premature stop codon mutation.

20. A method of treating Rett syndrome in a subject in need thereof, the method comprising administering to the subject a therapeutically effective amount of a compound represented by formula I:

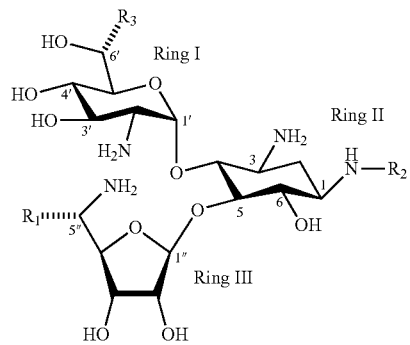

Formula I or a pharmaceutically acceptable salt thereof,
wherein:
$R_1$ is alkyl;
$R_2$ is hydrogen or (S)-4-amino-2-hydroxybutyryl (AHB);
$R_3$ is selected from the group consisting of hydrogen, alkyl, cycloalkyl and aryl;
a stereo-configuration of position 5" is an R configuration or an S configuration; and
a stereo-configuration of position 6', when chiral, is an R configuration or an S configuration,
said Rett syndrome being associated with a MECP2 premature stop codon mutation.

21. The method of claim 20, wherein said alkyl is methyl.

22. The method of claim 20, wherein $R_2$ and $R_3$ are each hydrogen.

23. The method of claim 20, wherein $R_2$ is AHB and $R_3$ is hydrogen.

24. The method of claim 20, wherein $R_2$ is hydrogen and $R_3$ is alkyl.

25. The method of claim 20, wherein $R_2$ is AHB and $R_3$ is alkyl.

26. The method of claim 25, wherein said alkyl is methyl.

27. The method of claim 20, wherein the compound is selected from the group consisting of:

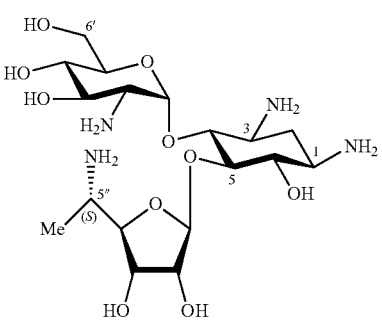

NB118

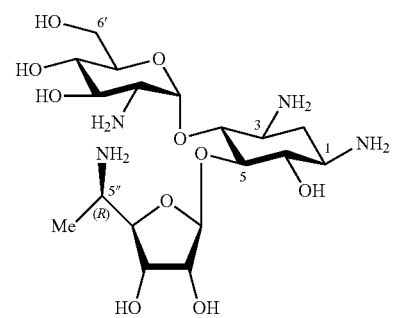
NB119
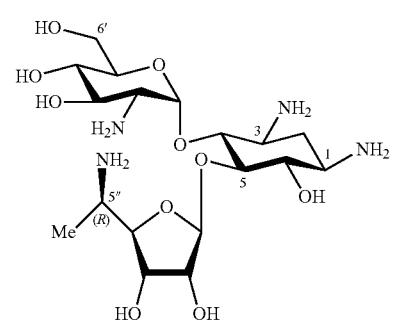
NB122
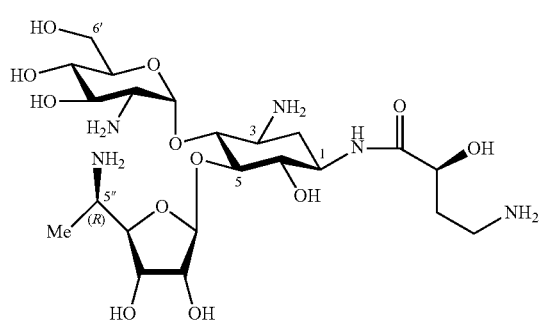
NB123
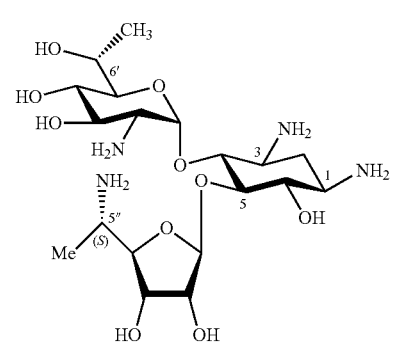
NB124
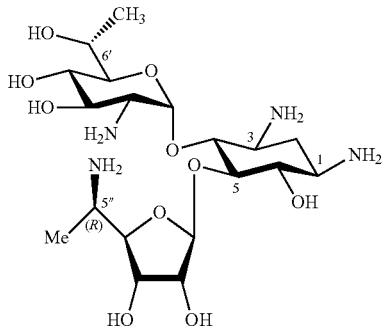
NB125
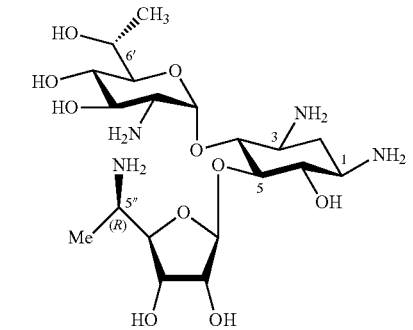
NB127
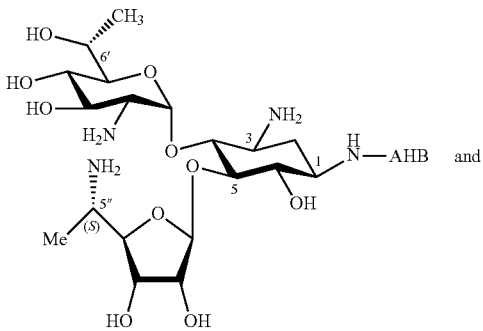
and
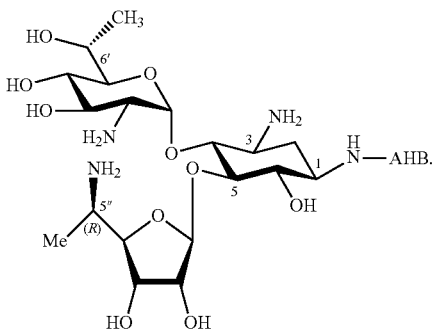
NB128.
28. The method of claim 20, wherein the compound is
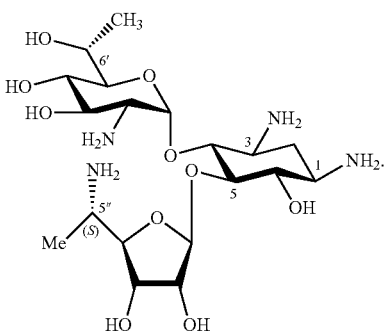
NB124.
29. The method of claim 20, wherein said mutation is a nonsense mutation.
30. The method of claim 29, wherein said MECP2 nonsense mutation is selected from the group consisting of R168X, R255X, R270X and R294X.
* * * * *